US009752984B2

(12) United States Patent
Verstegen et al.

(10) Patent No.: US 9,752,984 B2
(45) Date of Patent: Sep. 5, 2017

(54) ARRANGEMENT FOR AN ANALYSIS SYSTEM, ANALYSIS SYSTEM HAVING THE ARRANGEMENT AND METHOD FOR USE OF THE ARRANGEMENT

(71) Applicant: KONINKLIJKE PHILIPS N.V., Eindhoven (NL)

(72) Inventors: Emile Johannes Karel Verstegen, Eindhoven (NL); Adrianus Johannes Gerardus Mank, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 176 days.

(21) Appl. No.: 14/434,814

(22) PCT Filed: Oct. 17, 2013

(86) PCT No.: PCT/IB2013/059419
§ 371 (c)(1),
(2) Date: Apr. 10, 2015

(87) PCT Pub. No.: WO2014/060983
PCT Pub. Date: Apr. 24, 2014

(65) Prior Publication Data
US 2015/0260652 A1    Sep. 17, 2015

Related U.S. Application Data

(60) Provisional application No. 61/715,538, filed on Oct. 18, 2012.

(51) Int. Cl.
G01N 21/64        (2006.01)
G02B 27/28        (2006.01)
(Continued)

(52) U.S. Cl.
CPC ............ *G01N 21/64* (2013.01); *G01J 3/0224* (2013.01); *G01J 3/44* (2013.01); *G01N 21/645* (2013.01);
(Continued)

(58) Field of Classification Search
CPC ....... G01J 3/44; G01J 3/0224; G02F 1/13306; G02B 3/12; G02B 3/14; G02B 21/0092;
(Continued)

(56) References Cited

U.S. PATENT DOCUMENTS 6,134,010 A    10/2000 Zavislan
7,079,203 B1    7/2006 Huang et al.
(Continued)

FOREIGN PATENT DOCUMENTS

CN    101084049 A    12/2007
GB     958958 A       5/1965
(Continued)

OTHER PUBLICATIONS

Oemrawsingh et al: "Half-Integral Spiral Phase Plates for Optical Wavelengths"; J. Opt. A: Pure Appl. Opt. 6 (2004), pp. S288-S290.
(Continued)

*Primary Examiner* — Hina F Ayub
*Assistant Examiner* — Dominic J Bologna

(57) ABSTRACT

An arrangement having a birefringent component is provided for use in spatial offset measurements and analysis systems. The birefringent optical arrangement provides different directional control of the excitation signal relative to the emission signal, so that offset between an excitation and emission location on a sample can be controlled for both or only one of the excitation signal relative to the emission signal.

34 Claims, 20 Drawing Sheets

(51) Int. Cl.
*G02F 1/133* (2006.01)
*G01N 21/65* (2006.01)
*G02B 5/30* (2006.01)
*G01J 3/44* (2006.01)
*G02B 21/00* (2006.01)
*G01J 3/02* (2006.01)
*G01N 21/49* (2006.01)
*G02B 5/06* (2006.01)

(52) U.S. Cl.
CPC ......... *G01N 21/6445* (2013.01); *G01N 21/65* (2013.01); *G02B 5/3083* (2013.01); *G02B 21/0092* (2013.01); *G02F 1/13306* (2013.01); *G01N 21/49* (2013.01); *G01N 21/6458* (2013.01); *G01N 2201/0638* (2013.01); *G02B 5/06* (2013.01); *G02B 27/283* (2013.01)

(58) Field of Classification Search
CPC . G02B 5/04; G02B 5/045; G02B 5/06; G02B 5/3083; G02B 27/283; G01N 21/6445; G01N 21/645; G01N 21/65; G01N 21/64; G01N 21/6458; G01N 2201/0638; G01N 21/49
See application file for complete search history.

(56) References Cited

U.S. PATENT DOCUMENTS

| | | | |
|---|---|---|---|
| 7,706,071 | B2 | 4/2010 | Tang |
| 7,706,718 | B2 | 4/2010 | Karagiannis et al. |
| 7,738,095 | B2 | 6/2010 | Gardner, Jr. et al. |
| 7,909,958 | B2 | 3/2011 | Washburn et al. |
| 2007/0247635 | A1* | 10/2007 | Kruger .................. G02B 21/18 356/495 |
| 2007/0273943 | A1* | 11/2007 | Hendriks ................. G02B 3/14 359/32 |
| 2009/0009668 | A1* | 1/2009 | Tan ...................... G02B 5/3016 349/1 |
| 2009/0244692 | A1* | 10/2009 | Verstegen ................ G02B 3/14 359/315 |
| 2010/0264295 | A1* | 10/2010 | Van Dijk ........... G01N 21/6458 250/201.4 |

FOREIGN PATENT DOCUMENTS

| | | |
|---|---|---|
| WO | 2004059350 A1 | 7/2004 |
| WO | 2004059627 A1 | 7/2004 |
| WO | 2004059629 A1 | 7/2004 |
| WO | 2004070451 A1 | 8/2004 |
| WO | 2006003582 A1 | 1/2006 |
| WO | 2006052464 A2 | 5/2006 |
| WO | 2008126049 A1 | 10/2008 |

OTHER PUBLICATIONS

Oemrawsingh et al: "Production and Characterization of Spiral Phase for Optical Wavelengths"; Applied Optics, vol. 43, Issue 3, pp. 688-694, 2004.

MacLeod et al: "Deep Noninvasive Raman Spectroscopy of Turbid Media"; Applied Spectroscopy, vol. 62, No. 11, pp. 291A-304A, 2008.

MacLeod et al: "Deep Noninvasive Raman Spectroscopy of Turbid Media"; Applied Spectroscopy, vol. 62 (11), 2008, pp. 291A-304A.

* cited by examiner

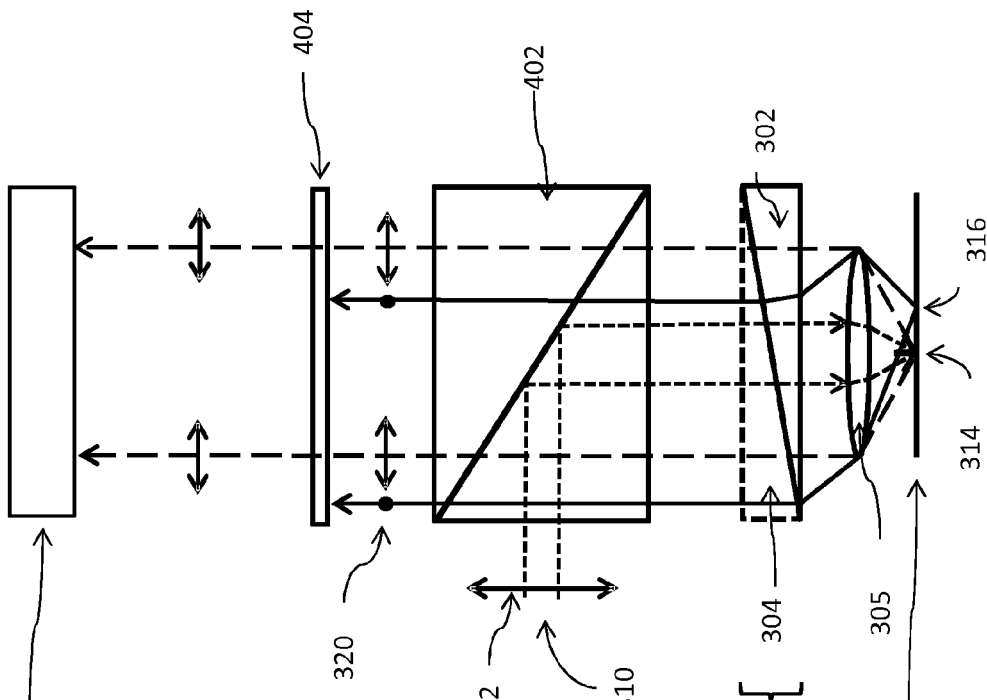
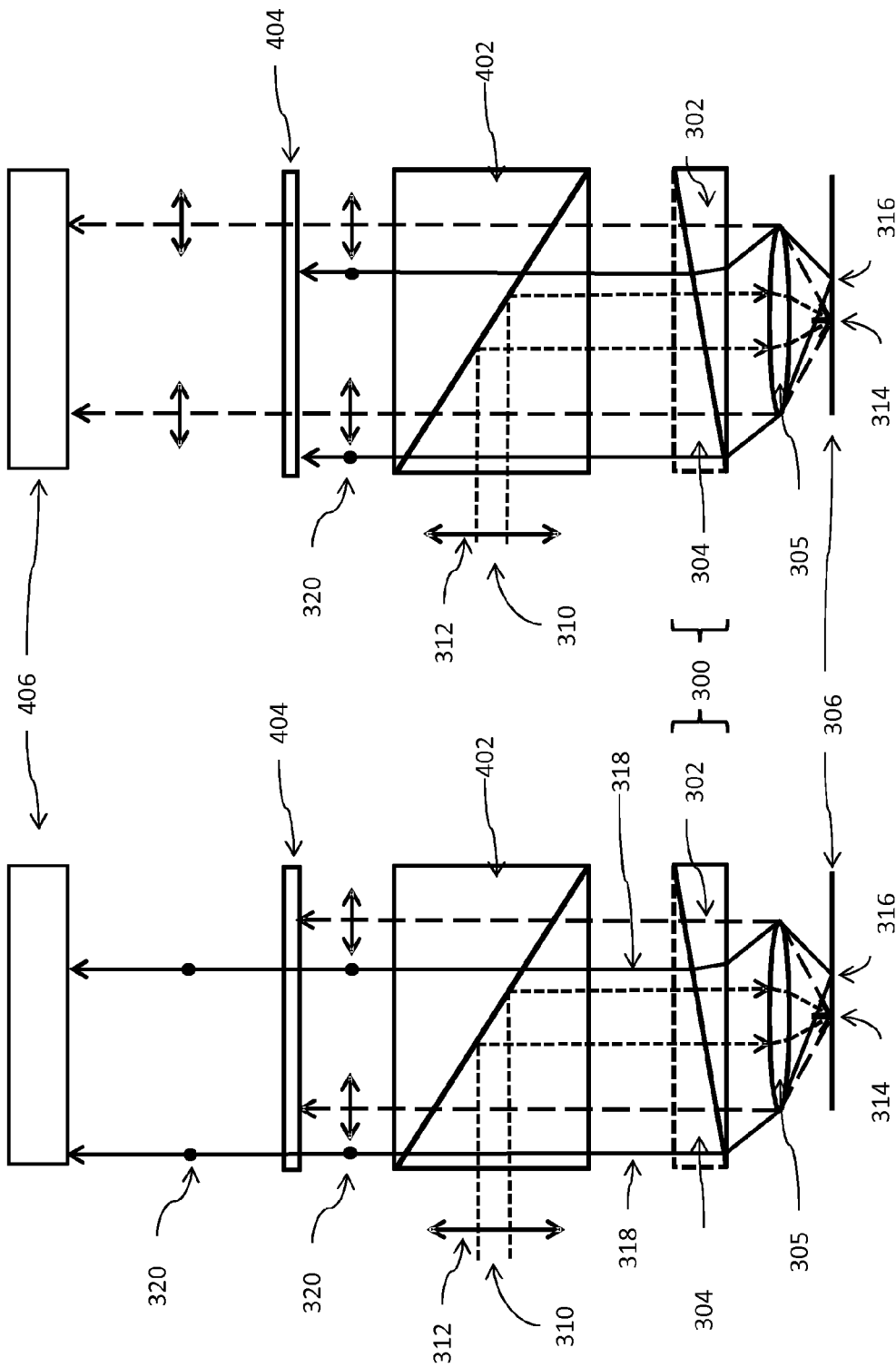

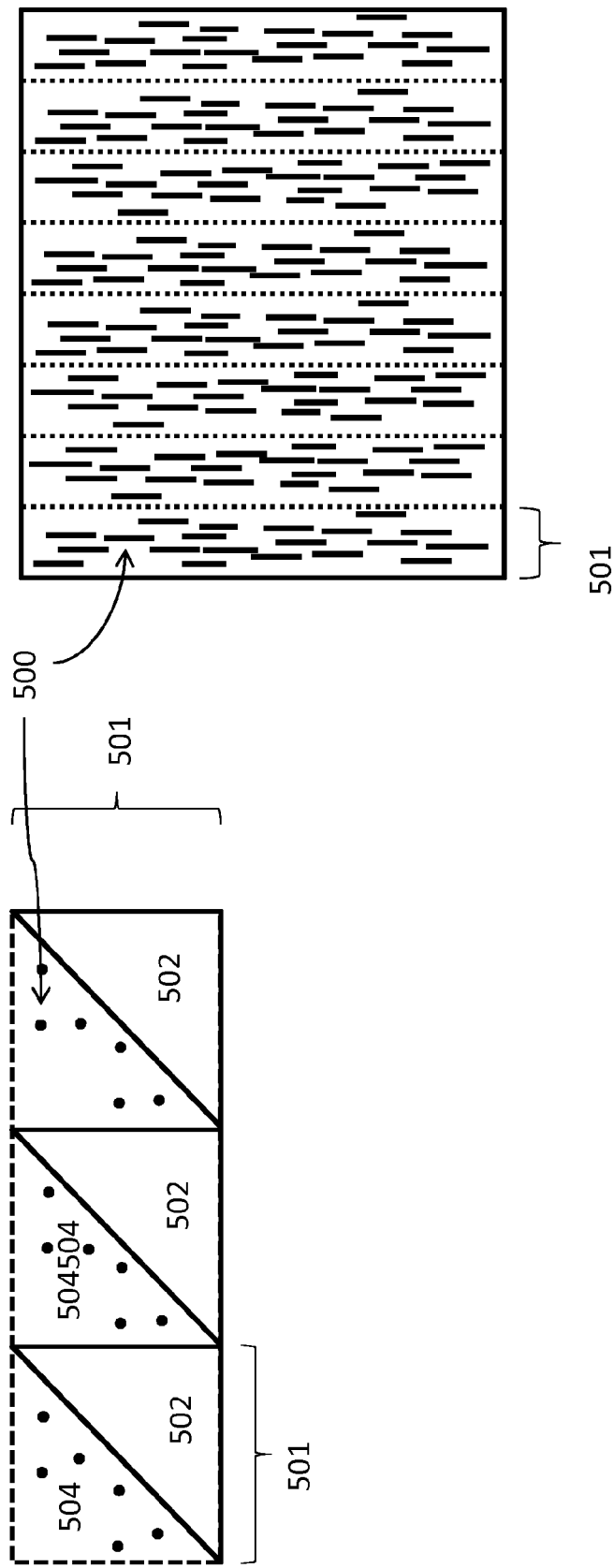

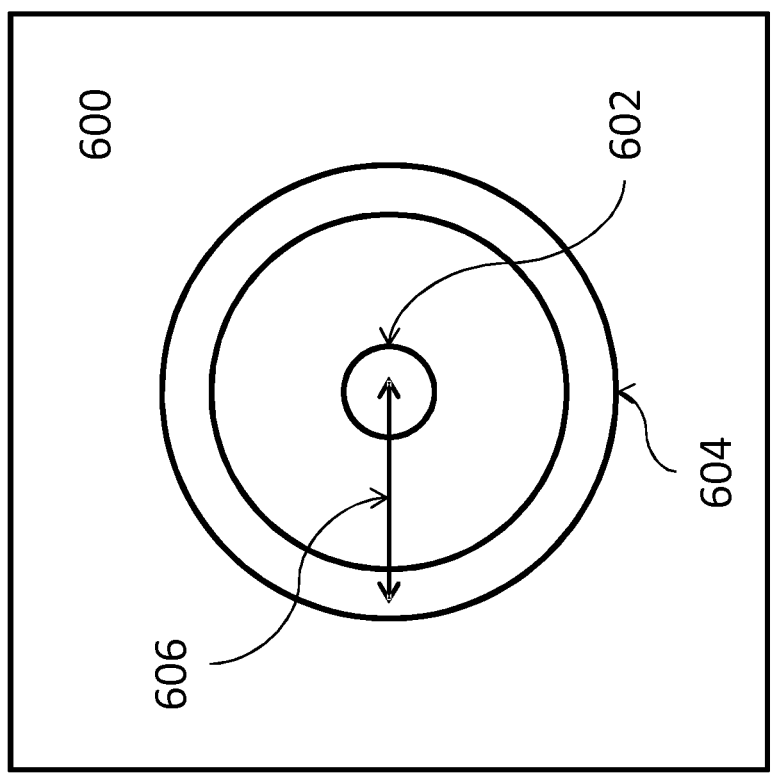

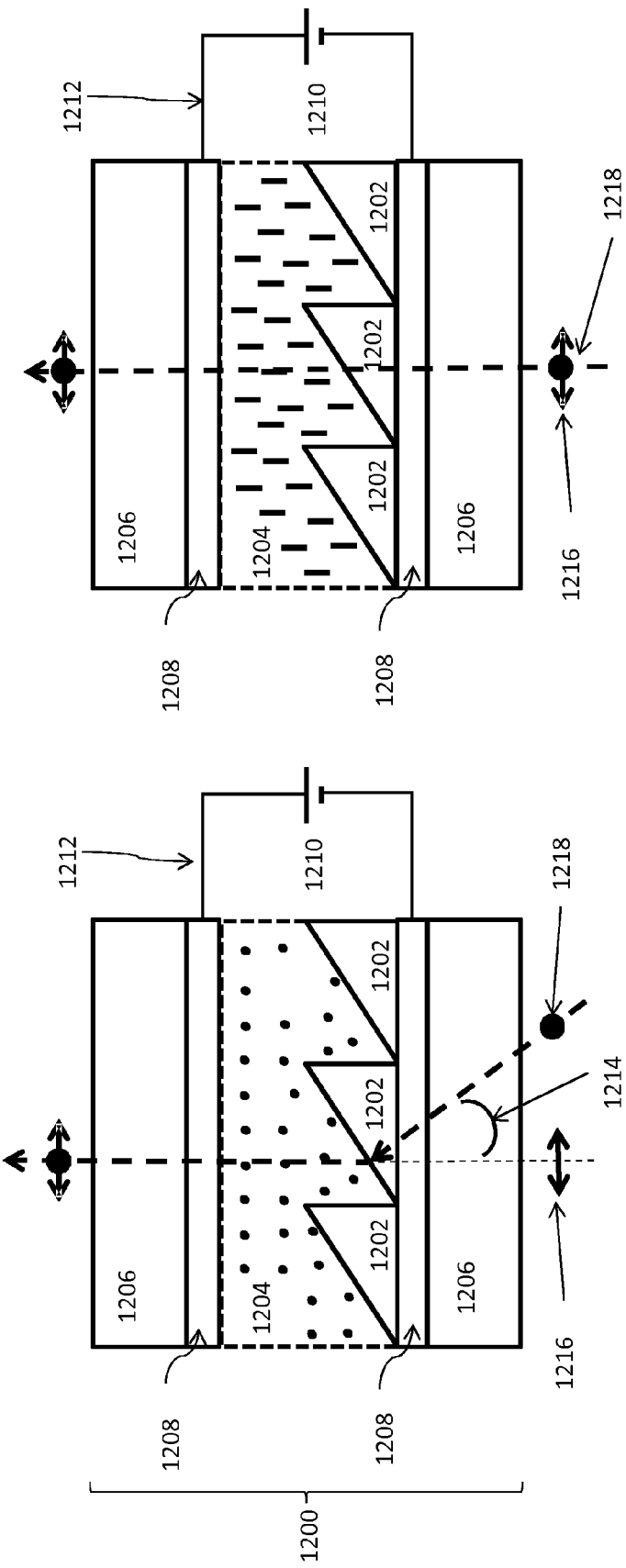

US 9,752,984 B2

ARRANGEMENT FOR AN ANALYSIS SYSTEM, ANALYSIS SYSTEM HAVING THE ARRANGEMENT AND METHOD FOR USE OF THE ARRANGEMENT

CROSS-REFERENCE TO PRIOR APPLICATIONS

This application is the U.S. National Phase application under 35 U.S.C. §371 of International Application No. PCT/IB2013/059419, filed on Oct. 17, 2013, which claims the benefit of U.S. Provisional Patent Application No. 61/715,538, filed on Oct. 18, 2012. These applications are hereby incorporated by reference herein.

FIELD OF THE INVENTION

This invention relates to an arrangement for use in spatial offset measurement, an analysis system having the arrangement and a method of spatial offset detection using the arrangement. In particular the invention relates to an arrangement, an analysis system and a method which involve excitation of a sample by means of an excitation beam and detection of a possible resulting emitted signal from the sample, which conveys information about the sample. The invention thus relates particularly to emission spectroscopy or inelastic scattering spectroscopy.

BACKGROUND OF THE INVENTION

Spectroscopic tools based on emission and detection of an optical signal are widely used to characterise, measure and/or detect components of a sample on the spot. Non-limiting examples of these optical signals are fluorescence, phosphorescence, Rayleigh scattering, Raman scattering and atomic emission signals. These tools offer the ability to measure directly on a defined spot in a non-contact fashion.

Raman analysis is based on inelastic scattering of excitation light by a sample to produce a spectrum of scattered light that is characteristic of the sample. The spectral lines are dependent on vibrational motion in the sample components and the probabilities of scattering. A sample consisting of a mixture of components results in a spectrum that is a linear combination of the component spectra. Hence, relative chemical content can be determined in a spectroscopic measurement using appropriate analysis of the spectrum. For more information on the nature of Raman spectroscopy the reader is referred to standard textbooks on Raman spectroscopy.

Conventional Raman spectroscopy is performed in backscatter mode wherein a sample spot is irradiated with excitation light and the backward scattered radiation is detected in the direct vicinity of the excitation spot. In a backscatter mode, the excitation beam and the resulting scattered optical signal travel through the same optical system, with optical splitting optics used to separate the emitted optical signal beam from the excitation signal beam, for example based on their different frequencies. Transparent or semi-transparent materials allow samples to be characterized beneath the sample surface (i.e. into the depth of the material of the sample) by performing measurements in the z-direction. However, although this type of depth analysis of samples is also desired when the material of interest is buried under a semi-, or non-transparent material such as a sheet of paper or a plastic cup for example, the conventional backscatter measurement is limited to the near-surface of such diffusely scattering objects. For example, with tissue it is limited to the first few hundred micrometers depth of surface material. Hence depth measurements are shielded and virtually impossible for non-transparent samples. The origin of this limitation is that the excitation signal intensity is high in the region of excitation so that it dominates the collected scattered radiation signal.

Spatially Offset Raman Spectroscopy (SORS) is a measurement variant that solves the above limitation in that it allows highly accurate chemical analysis of objects beneath obscuring surfaces, including for example tissue, coatings and packaging materials such as bottles. Examples of the fields of use of this SORS method include analysis of: bone beneath skin, contents inside plastic bottles for quality or composition control, security measurements as with detection of explosives inside containers and counterfeit practices such as with tablets inside blister packs.

The basic SORS method makes use of the fact that most sample materials are neither completely transparent to light, nor completely block it. Instead, they tend to scatter the excitation light much the same as when a red laser pointer illuminates the end of a finger, the light scatters throughout a large part of the tissue in the finger. Wherever the excitation light arrives in the sample, there will occur some inelastic scattering due to the Raman effect if Raman active materials are present in the sample. Thus, most parts of a sample, although not directly excited by the excitation spot, will generate a Raman signal, even if it is not at the surface of the sample. The SORS measurement is set up such that it avoids detection of scattered radiation at the dominating excitation region. Thus, more particularly, the SORS method is based on the collection of Raman spectra from regions away from the point of excitation on the sample surface, i.e. from regions that are spatially offset with regard to this excitation region. The spectra for laterally offset regions contain different relative contributions from sample layers located at different depths (z-direction) in the sample material. This difference is brought about by a wider lateral diffusion of photons emerging from greater depths of the sample.

Thus, by making at least two Raman measurements, one at the surface and one at an offset position of typically a few millimeters away and by subtracting these spectra using a scaled subtraction, two spectra can be produced of which one represents the subsurface (interior of the sample) and the other represents the surface. For a simple two-layer system, such as powder in a plastic bottle, the powder spectrum can be measured without knowing the bottle material or its relative signal contribution. To do this without using an offset measurement would be severely restricted by photon shot noise generated by Raman and fluorescence signals originating from the surface layer.

A further useful sub-variant of SORS that improves certain measurements such as analysis of tissue in vivo is Inverse SORS. Rather than use a spot collection geometry and a circular spot for illumination, the constant offset is maintained by exciting the sample with a ring of light centred on the collection region.

Although scaled subtraction of spectra works well for two-layer samples, samples with more complicated compositions, such as where the overlying material contains components included in the sub-layer as in living tissue, for example, may require multi-variate analysis (e.g. Principal Component Analysis). This in turn means however that it is necessary to take several spectra at different offset distances. In the different spectra, as the spatial offset increases, also the ratio of the spectral contribution sub-surface/surface increases, providing again a separation of components using the multi-variate analysis. The limit for this is given by the fact that the total detected signal also decreases with increasing offset, so that the maximum has to be offset against signal to noise ratio in a practical measurement.

The devices capable of measuring SORS spectra rely on complicated excitation detection devices often in combination with movable stages for measuring the spectra at variable offsets. Such devices are difficult to use in application fields where measurements are performed on the spot.

In conventional Raman spectrometers the locations of excitation and detection are fixed by the optical system and in most systems these locations exactly overlap (backscattering configuration). Therefore it is difficult to implement SORS in conventional Raman systems without costly and extensive redesigns. Hence there is a need for simplified equipment that is robust yet does provide the flexibility to perform the offset measurements at variable offsets.

SUMMARY OF THE INVENTION

It is an object of the invention to provide spatially offset detection or analysis in a less complicated way at least reducing any one or more of the above mentioned difficulties.

The object is achieved by the invention as defined by the independent claims. The dependent claims provide advantageous embodiments.

The invention defines an arrangement for use with spatial offset detection and/or analysis, an analysis system including the arrangement (integrated or as an accessory) and a method of using the arrangement for performing spatial offset detection and/or analysis. Definitions and advantages described herein below relate to all three aspects of the invention unless otherwise specified.

Spatial offset detection or analysis, can be defined as the excitation of a sample or medium with primary radiation on a first location on that sample or medium, wherein the primary radiation is suitable for causing a medium to potentially emit secondary radiation, and subsequently collection of secondary radiation from a second location on the sample or medium that is at least partially different from the first location. The invention is based on the idea that such detection or measurement can be done in a simplified way using a birefringent component which allows to perform the excitation with primary radiation of a first polarisation at a first location while allowing collection of the secondary radiation of a second polarisation that is different from the first polarisation at another location.

This is because, a birefringent component manipulates radiation with different polarisation differently due to its anisotropic properties of its interaction with radiation if the propagation direction of radiation is not oriented either parallel or orthogonal to the axis of anisotropy (optical axis). In such cases the birefringent component is capable of splitting a beam of randomly polarised radiation into two beams of orthogonally polarised radiation. One such split beam path can thus be used for manipulating excitation radiation while the other path can be used to manipulate emitted radiation.

This makes that a simple arrangement can be used to provide spatial offset capability and, even a capability to move and/or shape the different beams relative to another without having to provide complex mechanical stages etc, when the birefringent component can be interchanged or adjusted.

The first and second polarisation can be any type of polarisation ranging from circular, elliptical to linear. Preferably the polarisations are linear and/or orthogonal to each other. In case of circular polarisation, the rotation direction of the first and second polarisation may be opposite. It is noted that in agreement with this, radiation impinging on the arrangement may still be of randomly polarised/unpolarised nature as the arrangment will split it into the first and second polarisation to be treated as desired.

A medium (also called a sample) can be any material to be analysed. The invention is particularly suitable for interior (volumetric) analysis of media that have reduced transparency, or are non-transparent (e.g turbid) for the primary radiation and/or the secondary radiation. Such media may be gaseous, or in vapour phase, but preferably are liquid or solid. The media do not have to be homogeneous. This will be further elucidated in the description of the invention.

The first location and/or the second location on the medium may be on the surface of the medium, but also within the volume spanned by the medium. If the medium is relatively non-transparent, the locations can preferably refer to areas on the surface of the medium. The locations may also refer to a volume in the medium. The area and volume may have any shape. These characteristics of the first and or second location hold also for other locations such as a third location on the medium if specified in any claim. The term that the locations are at least partially different means that such locations can overlap but only to such extent that at least one of the locations has a part that falls outside the other location. The locations can also not overlap at all.

In any of the embodiments of the invention, the directing of a beam of primary radiation, and/or the directing of the part of the beam of secondary radiation, and/or the first manipulation and/or the second manipulation can comprise or consist of different types of beam shaping. Such types of beam shaping include: changing the parallelism of a beam of radiation (e.g. divergence, or convergence, or focussing), and/or beam shaping with respect to the cross section of the beam (e.g. from circular to ring shaped, form square or circular to line shaped, from closed circle to open circle or vice versa) and/or beam steering (deflection, reflection or refraction of the beam propagation direction). In any of the embodiments of the invention, each of the above parameters can mean that a beam is effectively passed unaltered by the arrangement and/or the birefringent component. Thus, a beam of radiation can be directed by the arrangement and/or manipulated by the birefringent component such that it does not change shape and/or cross section and/or propagation direction.

In case the radiation impinging on the birefringent component is randomly polarised, a split beam of radiation of first polarisation results which are manipulated such that they end up in a first location actually comprising two split sub-locations. This is however not a problem as the resulting beams of radiation with second polarisation will stem from corresponding sub-locations and be manipulated correctly again after reimpinging on the birefringent component.

The radiation preferably is optical radiation, which is understood to include ultraviolet radiation (UV), the spectrum of light visible for man (VIS) near infrared radiation (NIR) and infrared radiation (IR). Optical radiation ranges between wavelengths of approximately 1000 nm to 1 mm. Such radiation types do not require large setups for generation such that large impractical devices would be needed to deploy the invention. The secondary radiation may have a wavelength range that is shifted with respect to the wavelength range of the primary radiation due to the interaction with a medium during excitation with primary radiation. The shift can be to higher wavelength as caused by frequency doubling, or two-photon fluorescence, but generally is to lower wavelength as with IR, RAMAN, or UV or phosphorescence. The ranges can comprise different width. Preferably the primary radiation is light suitable to generate secondary radiation with a wavelength range forming a spectrum. This allows analysis in the form of spectroscopy giving fingerprinting opportunity of the medium. Examples are IR or RAMAN spectroscopy providing convenient ways to determine medium composition. Alternatively, the primary radiation is light of a suitable wavelength to generate fluorescence and or phosphorescence radiation as the secondary radiation.

The arrangement can consist of the birefringent component as the sole component for radiation manipulation. In that case the directing of the beam of primary radiation as also the directing of the beam of the secondary radiation is provided by the first manipulation and the second manipulation respectively. This embodiment can still have features for attaching the arrangement to an analysis system, for holding or manipulating the birefringent component and those further defining the birefringent component as defined herein below.

The birefringent component can have a birefringent refractive surface at which there is a difference between at least one of the refractive indices of a birefringent material and another material.

The birefringent material can comprises an ordinary refractive index and an extraordinary refractive index therewith defining a birefringent surface with a further material having a further refractive index that is different from at least one of the ordinary refractive index and the extraordinary refractive index, wherein the birefringent surface is for providing the first manipulation and/or the second manipulation. The further material need not be part of the arrangement. It may be the surrounding of the arrangement such as air, nitrogen or any another gaseous medium. With the shape of the birefringent surface, the first and or second manipulation can be defined such as e.g. convergence or divergence by a curved surface in the form of a mirror or lens and such as e.g. deflection by a mirror or refraction by a prism shaped surface. Combinations of these are possible. The further material may also be a birefringent material. It may even be the same birefringent material, as long as the optical axes of both birefringent materials are not oriented parallel.

The further material can be part of the birefringent component. If the further material is part of the birefringent component such that it defines the birefringent surface, then its optical properties can be controlled through its composition and/or its orientation with respect to the further material. In a preferred option, the further material has a refractive index that is equal with at least one of the ordinary and extraordinary refractive indices of the birefringent material. This allows that for one of the polarisations, a beam of radiation can pass the birefringent component unmanipulated as it experiences no refractive index difference at the birefringent surface. Hence, the arrangement allows that during analysis one location can be kept constant while the other location can be varied. Variation can be effectuated by changing of the birefringence of the component (see herein below), and/or changing the orientation of the optical axis of the birefringent material with respect to the propagation direction of the beam of radiation for which a different manipulation effect is desired.

In order to have control over the directing of a beam of radiation by the arrangement such that the first and second locations can be altered relative to each other, preferably the birefringent component is controllable for adjustment of the first manipulation and/or the second manipulation. The control can comprise adjustment of a first and or second manipulation to change, or adjust between different types of beam shaping (see herein above), and/or to change or adjust the extent to which a particular type of beam shaping is performed. Such control can be obtained using any one of a number of beam control options in the invention.

With a first beam control option the birefringent material comprises a liquid crystal material and at least one electrode for applying an electric field over at least a part of the liquid crystal material for controlling the adjustment of the first manipulation and/or of the second manipulation. In practice usually more than one electrode is used to apply electric fields over the birefringent materials. A liquid crystal material is a birefringent material of which the orientation of its optical axis can be changed under influence of an electric field applied to the birefringent material. Hence, the birefringence experienced by the different beams at a birefringent surface can be altered by adjusting the voltage supplied.

In one example, the birefringent component comprises a liquid crystal based GRaded INdex (GRIN) device. In such a device there are multiple electrodes arranged such that by application of a specific voltage pattern to the electrodes the electric field in the liquid crystal material comprises a field such that part of the liquid crystal material molecules orient parallel to the field lines while the other liquid crystal material molecules do not orient or to a lesser extent, therewith forming a layer with graded refractive index functioning as a birefringent surface (or layer with graded index differences) between the oriented part and the substantially non-oriented parts. In this way liquid crystal based adjustable birefringent GRIN lenses are conveniently made that have adjustable lens strength and/or lens shape.

With a further beam control option the birefringent component can be used in combination with a polarisation adjustment component for adjusting the polarisation of primary radiation of the beam of primary radiation before the primary radiation is incident on the birefringent component. Change of polarisation direction (e.g rotation of the polarisation of primary radiation) with respect to the optical axis of the birefringent component can change the first manipulation. Hence, the first location can be changed by changing the first polarisation. The polarisation of the secondary radiation can be left unaltered if the secondary radiation does not pass the polarisation adjustment component after collection by the birefringent component. However, it may also pass the polarisation adjustment component because it has already been manipulated by the birefringent component, so that its adjustment by the polarisation adjustment component does not affect the first location anyway. The polarisation adjustment component can be a half wave plate. Preferably it is a component based on flat liquid crystal device such as e.g that of a non-patterned or non-pixelated liquid crystal Display module (without the backlight). This example is advantageous as at the expense of an extra component, the birefringent component itself does not need to have a more complicated construction for containing a liquid crystal material or any other exchangeable material for implementing the beam control option.

In a further beam control option the birefringent material comprises an ordinary refractive index and an extraordinary refractive index and the birefringent component comprises a further material having a further refractive index that is different from at least one of the ordinary refractive index and the extraordinary refractive index, wherein the birefringent material and the further material define a birefringent surface for providing the first manipulation and/or the second manipulation, wherein the further material comprises a solid material for defining the shape of the birefringent surface and wherein the birefringent material comprises a liquid crystal material and the arrangement comprises at least one electrode for applying an electric field over at least a part of the liquid crystal material for controlling the adjustment of the first manipulation and/or of the second manipulation. In this case the birefringent component comprises a replica material that defines the shape of the birefringent surface facilitating fabrication. In practice usually more than one electrode is used to apply electric fields over the birefringent materials. This enables that orientation of the liquid crystal material at the birefringent surface can be effectuated giving the control.

In yet another beam control option the birefringent material comprises an ordinary refractive index and an extraordinary refractive index and the birefringent component comprises a further material having a further refractive index that is different from at least one of the ordinary refractive index and the extraordinary refractive index, wherein the birefringent material and the further material define a birefringent surface for providing the first manipulation and/or the second manipulation, wherein the birefringent material comprises a solid material for defining the shape of the birefringent surface and wherein the further material comprises a fluid material contained within a compartment having a boundary formed by the birefringent surface such that the fluid material is in contact with the birefringent material, wherein the composition of the fluid material in contact with the birefringent material is adjustable. In this embodiment so called electrowetting lenses can be used for providing the beam control. The further material before change has a refractive index different from that after its change.

In the invention, the birefringent surface can comprise a shape such that the first manipulation and/or the second manipulation comprise deflection and/or change of parallelism of a beam of radiation. Preferably, the birefringent surface comprises a birefringent prism surface for providing the deflection and/or a birefringent lens surface for providing the change of parallelism of a beam of radiation. This latter example allows use of transparent birefringent components instead of e.g. mirror type devices. With the shape of the surface a type of beam control can be obtained. Thus, a lens shape may give divergence, convergence or focussing as described herein above. A prism shape can provide beam deflection.

In a particular embodiment of the invention, the birefringent surface comprises a plurality of birefringent sub-surfaces such that for each of the birefringent sub-surfaces it holds that:
   the birefringent sub-surface contains an imaginary radial line extending radially from an axis, the axis being oriented perpendicular to a imaginary plane;
   the birefringent sub-surface is inclined with respect to the imaginary plane over an inclination angle, the inclination angle being defined between an imaginary line that is either contained by the birefringent surface or is the tangential line to the birefringent surface, the imaginary line being perpendicular to the imaginary radial line, and the line constructed by perpendicular projection of the imaginary line onto the imaginary plane. The surface can be that of a spiral plate having sub-surfaces that resemble steps of a spiral staircase around an axis. The sub prisms preferably are located at different distance along the axis as measured from an origin. In this way a spiralling prism is formed. The distance related to one rotation of the spiral around the axis can be varied for different spiral plates. With such a device a beam with a second polarisation and having solid cross section can be transferred in a beam with open cross section, while the beam with first polarisation remains to have a solid cross section lying inside the open circle. Hence a medium can be excited at a middle spot while excitation can be gathered around it. This may increase sensitivity of the device.

According to the invention use can be made of a further birefringent component and the directing of the beam of the primary radiation comprises a further first manipulation by the further birefringent component and the directing of the at least part of the collected beam of secondary radiation comprises a further second manipulation by the further birefringent component, wherein the effect of the further first manipulation is different from the effect of the further second manipulation due to the first polarisation being different from the second polarisation. Here there may be a lens and/or a prism etc. The birefringent component and the further birefringent component can be made so as to be integrated into a compound component much like a compound lens. The arrangement can have birefringent component that is not necessarily made of one single birefringent component, although this is preferred for ease of manufacture or deployment. It may comprise multiple separate birefringent components that possibly can also be separately controlled to give separate manipulations. The separate birefringent components may be located such that they transmit both at least one of the beams of primary and secondary radiation. Alternatively, they may be arranged such that one transmits the beam of primary radiation while the other transmits the beam of secondary radiation.

The birefringent component can be used in combination with a pinhole component comprising a pinhole for passing at least part of the beam of secondary radiation. Limiting the cross section of the beam of secondary radiation reaching the detector can be used to increase contrast for the second location from which secondary radiation is collected. There may be pinhole for the beam of primary radiation also. Alternatively or additionally, the pinholes of the component may be used to define the shape (cross section) of the beams of the primary and/or the secondary radiation. Moreover, the pinholes can also be used to fix or limit the area of the locations of which the birefringent component is able to direct the beam of secondary radiation to the detector.

The birefringent component can be used in combination with a collection component for convergence of the at least part of the beam of the secondary radiation. This again improves contrast for the second location and also increases the sensitivity of the measurement. The component preferably is a lens that operates as an objective. Preferably the objective is located at the side of the birefringent component where also the medium would be located. The component may be integrated in the birefringent component when the birefringent component is a lens. Hence no additional lenses are needed.

The birefringent component can be used in combination with a beam splitter arranged in between the birefringent component and the detector, the beam splitter being arranged for passing the at least part of the beam of the secondary radiation towards the detector and for directing any primary radiation directed by the birefringent component to the beam splitter away from the detector. The beam splitter can be a wavelength dependent beam splitter such as a notch filter (reflector) or edge filter (reflector). It can be a half transparent prism etc. Any primary radiation picked up by the birefringent component and directed in the direction of the detector can be split off by the beam splitter, while the beam splitter can also be used to provide the primary radiation to the birefringent component. Microscopes such as e.g. backscatter microscopes often already include such a beam splitter that can be advantageously used in combination with the birefringent component.

The birefringent component can be used in combination with a polarisation selective filter arranged in between the birefringent component and the detector for controlling the intensity of the secondary radiation that is incident on the detector. If the arrangement of the invention is further capable of directing at least a part of a beam of secondary radiation of the first polarisation, collected from the first location towards the detector, then the polarisation selective filter can be used to record successive detection of secondary radiation signals with mutually different composition with respect to relative composition of secondary radiation originating from the first location and that originating from the second location, as these two will have different polarisation. The two recordings allow that no reference data of the medium (sample) surface signal are needed for determining the nature of a layer of the medium behind the surface layer. Alternatively, the polarisation selective filter can be omitted and a further detector for detecting secondary radiation of the first location can be used such that secondary radiation of the second location is directed towards the detector while secondary radiation of the first location is directed towards the further detector. At the expense of a further detector now simultaneous measurement can be done.

The arrangement can be configured such that the birefringent component can be removed from and attached to or inserted in it. Preferably, the arrangement comprises a holder for holding the birefringent component, wherein the holder is removable from the arrangement. This allows that the arrangement can remain attached to, or part of an analysis system while the birefringent component can be removed or replaced with another one. Hence, the spatial offset detection mode can be switched off by removal of the birefringent component from the relevant beams of radiation, removed from the arrangement entirely. Also the spatial offset detection mode can be adjusted to provide other modes of spatial offset detection by replacement of a birefringent component or even addition of one or more birefringent components.

The holder can be configured for holding a plurality of birefringent components. The holder can comprise several sub holders each one for holding at least one birefringent component. Preferably a holder or the sub-holders are moveable with respect to the arrangement such that one or more birefringent components can be positioned in the primary and/or secondary beam of radiation to provide the first manipulation and/or the second manipulation at any one time. The holder and/or sub-holder can be a sliding holder or carousel holder with all advantageous of adaptation of the birefringent component to the spatial offset detection needed at any one time. The holders can be manually operable or electrically operable if electro servo motors and transmission devices are present.

The arrangement can have the form of an accessory for an analysis system that can be detachably attached to the analysis system. Attachment means can be based on parts having screw thread, possibly fitting such screw thread as used to screw objective lenses in an objective holder carousel of a microscope. Alternatively, attachment means can be based on bayonet connections or magnetic connections etc. With the accessory type attachment, regular analysis systems such as microscopes, backscatter microscopes, spectrometers and other devices can be provided with spatial offset detection capability with relative simplicity. The field of use of such regular devices can thus be conveniently extended into the field of spatial offset detection, without having to add complicated moving parts to such regular devices.

The arrangement can have an operating mode in which the first location and the second location are the same. In this way spatial offset function of the arrangement can be turned off such that an analysis system capable of other measurements (microscopes etc.) can return to perform these other analyses. The operating mode can be implemented through an arrangement having a configuration for: removing the birefringent component from the locations in which it is capable to provide first and/or second manipulations; and/or for controlling the birefringent component to a state wherein the first manipulation is the same as the second manipulation.

In the latter case a birefringent component having a liquid crystal material as defined herein is advantageous as those allow to switch the liquid crystal layer such that the directors are parallel to propagation direction of the beam of the primary radiation and the beam of the secondary radiation if these are parallel. For example, the birefringent component having a liquid crystal layer may have transparent electrodes on either side of the liquid crystal material such that orientation of the liquid crystal molecules upon application of an electric field becomes parallel to the propagation direction of the beams of primary and secondary radiation.

The arrangement of the invention can be used to advantage for performing spatially offset analysis. In particular the arrangement can be used with an analysis system. Preferably, the use provides the analysis system with the spatial offset measurement capability that it would not have without the arrangement. The analysis system preferably comprises or consists of any one, or a combination of: a microscope, a backscatter microscope, a fluorescence detection system, a phosphorescence detection system, a RAMAN spectrometer, a near-IR and/or IR spectrometer, a UV spectrometer, a microwave detection system. The field of use of such abundantly available systems can be conveniently and with relatively low cost equipped with capability for spatial offset analysis. The use can be for product quality check after packaging or for customs check purposes.

The arrangement of the invention is preferably configured for allowing that the beam of primary radiation has a first beam propagation direction when it is incident on the birefringent component and the at least part of the beam of secondary radiation has a second beam propagation direction when it exits the birefringent component, wherein the first propagation direction and the second propagation direction are parallel and opposite to each other. Such an arrangement can be conveniently used in a backscatter microscope.

The arrangement can be very effectively used in an analysis system especially in optical analysis system such as e.g. a microscope, a backscatter microscope, a fluorescence detection system, a phosphorescence detection system, a RAMAN spectrometer, a near-IR and/or IR spectrometer, a UV spectrometer, a microwave detection system. The microscope or backscatter microscope can be a part of the detection systems or the spectrometers. Preferably the arrangement forms an accessory to such analysis system as then the field of use of the analysis system can be extended with the spatial offset detection functions the arrangement provides.

The analysis system can already comprise specific parts of an arrangement as defined herein. In particular an analysis system can already comprise:

a beam splitter arranged in between the birefringent component and the detector, the beam splitter being arranged for passing the at least part of the beam of the secondary radiation towards the detector and for directing any primary radiation directed by the birefringent component to the beam splitter substantially away from the detector and the beam splitter being further arranged for directing the primary radiation from the source to the birefringent component;

a polarisation adjustment component for adjusting the polarisation of the primary radiation before the primary radiation is incident on the birefringent component; and a polarisation selective filter arranged in between the birefringent component and the detector for controlling the intensity of the secondary radiation that is incident on the detector. The analysis system then advantageously combines with an arrangement of the invention that is an accessory to the analysis system, but that does not comprise the beam splitter, the polarisation adjustment component and the polarisation selective filter as these are already present in the analysis system. Generally microscopes and backscatter microscopes are such analysis systems.

The collection component in the form of e.g. a microscope objective can be part of the analysis system and can be reused to be attached to the arrangement. The arrangement therefore may have screw thread matching the screw thread on the objective or collection component.

The analysis system further can comprise a unit for data analysis of spatial offset detection measurements. Hence the detected data of the secondary radiation can be used to reveal the medium composition.

The invention provides a method of performing spatial offset detection, the method comprising:

providing an arrangement as claimed in any one of the claims 1 to 21;

providing a primary radiation for causing the medium to emit a secondary radiation when irradiated with the primary radiation, the primary radiation comprising a first polarisation;

directing a beam of the primary radiation of the first polarisation towards a first location on the medium;

directing at least a part of a beam of the secondary radiation of a second polarisation, collected from a second location on the medium, towards a detector for detecting secondary radiation, the second location being at least partially different from the first location;

wherein the directing of the beam of the primary radiation comprises a first manipulation by the birefringent component and the directing of the at least part of the collected beam of the secondary radiation comprises a second manipulation by the birefringent component, wherein the effect of the first manipulation is different from the effect of the second manipulation due to the first polarisation being different from the second polarisation.

The method can have additional steps comprising directing at least a part of a beam of secondary radiation of the first polarisation, collected from the first location towards a further detector for detecting secondary radiation, wherein directing the at least part of a beam of secondary radiation of the first polarisation comprises a third manipulation by the birefringent component wherein the effect of the third manipulation is different from the effect of the second manipulation due to the first polarisation being different from the second polarisation.

This method allows obtaining secondary radiation from two locations on the medium, i.e. the second location and the first location with only one configuration of excitation, as for the two data points no location changes have to be performed. The two datapoints allow deduction of composition of the medium in two depth layers, one of which represents the surface (first location data) and one of which represents inner part of the medium. No reference data for the surface need be known.

Preferably, the further detector is the same as the detector, and wherein the arrangement comprises a polarisation selective filter for adjusting the relative contribution of secondary radiation of the first polarisation and the secondary radiation of the second polarisation incident on the detector, between consecutive detections of secondary radiation. This allows that the two point measurement method can be performed on a regular analysis system such as a microscope without requiring extra detectors. In the method, after direction of the secondary radiation by the birefringent component towards the detector for the detection of the secondary radiation one can make use of the same optical path for both the secondary radiation of the first polarisation and that of the second polarisation. No extra detector is needed. To filter or change the relative content of secondary radiation from the first and second location, the polarisation selective filter needs to be adjusted between successive measurements of the secondary radiation. Both datapoints can again be used to obtain data on the surface of the medium and a deeper layer.

In the method an arrangement as claimed in claim 4 can be used. This allows the method to comprise the further steps of:

detecting secondary radiation with the second polarisation from the second location, controlling the birefringent component to shift the second location while keeping the first location constant detecting secondary radiation with the second polarisation from the shifted second location.

The more data points can be obtained, the better a depth profile behind the surface of the medium can be determined. In this case no moving parts are needed for such measurements as the birefringent component can be controlled to give relative movement of the beam of secondary radiation with respect to the beam of the primary radiation.

The data points herein preferably are spectra representative of a material, such as UV, fluorescence, RAMAN or IR spectra.

BRIEF DESCRIPTION OF THE FIGURES

All Figs. are schematic drawings unless otherwise indicated.

FIGS. 4A and 4B each show the arrangement of FIG. 3 further including radiation beam splitters and filters.

FIGS. 5A and 5B show side and top views of an implementation of a prism.

FIG. 6 shows a top view of the radiation excitation and collection pattern on a medium obtainable with a spiral plate.

FIGS. 12A and 12B show a birefringent prism with adjustable birefringence based on liquid crystal layer and how it's birefringence can provide different operating modes.

DETAILED DESCRIPTION OF EMBODIMENTS

Figure 1:
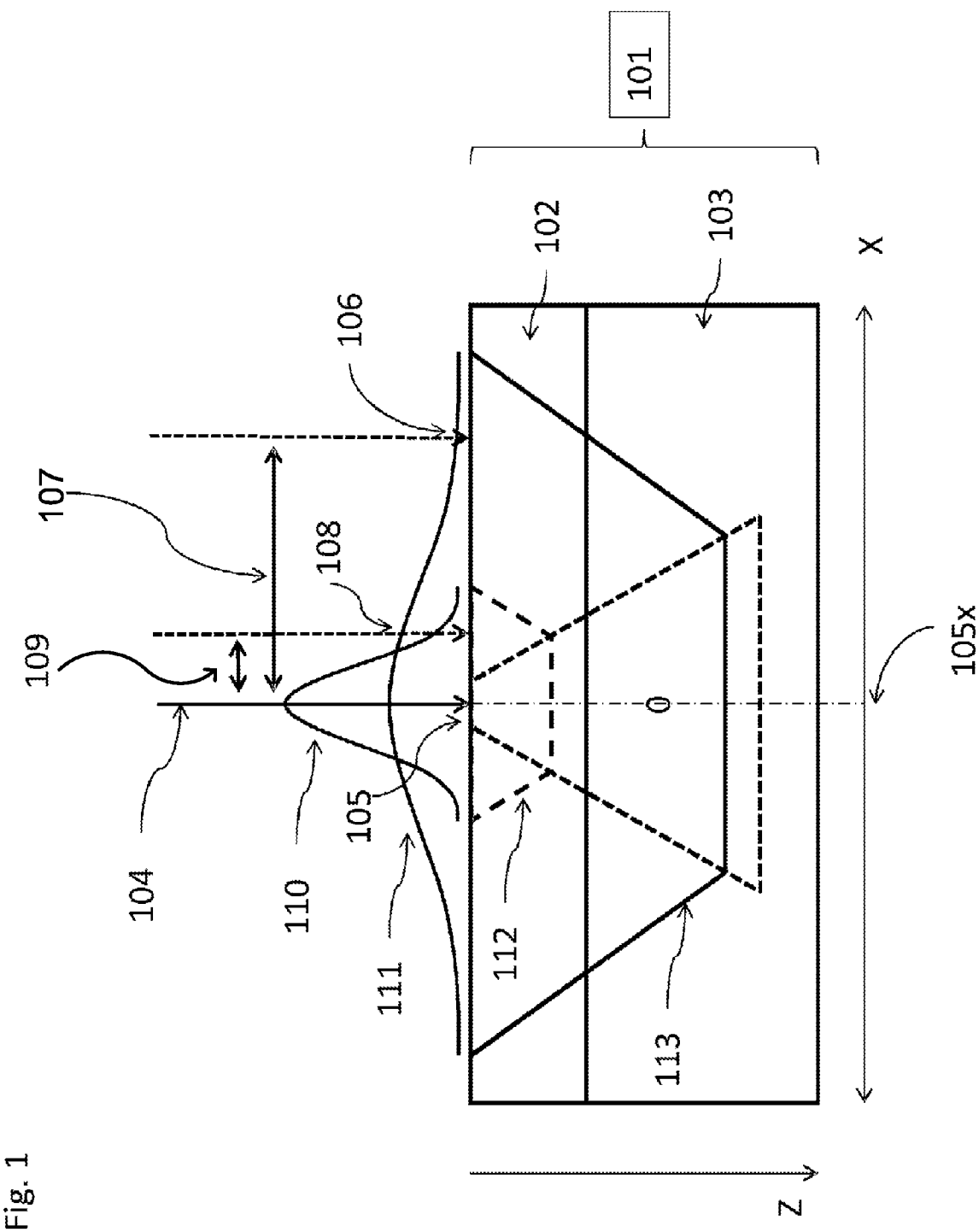
FIG. 1 shows a cross sectional view of a sample with the depth direction (Z-axis) as the vertical in the plane of drawing. It is used to indicate how excitation of a medium with excitation radiation at one location on a medium leads to emission of radiation at other locations.

The invention provides a general solution to the need for independent control of the characteristics of an excitation beam of radiation and an emission beam of radiation in an analysis system such as a spectroscopy system, preferably without using moving parts, for the purpose of enabling Spatially Offset detection such as SORS. In the context of this invention spatially offset measurements relate to controllable offset between excitation location and emission collection location where offset relates to depth difference and/or lateral sample surface difference. The arrangement of the invention allows easy adaptation of existing analysis systems to enable such measurements.

The term refractive index is applicable to the full electromagnetic spectrum and in particular to the optical part of the spectrum.

Birefringence is the property of a material having a refractive index that depends on the polarization and propagation direction of light. An anisotropic material is said to be birefringent. The birefringence is often quantified by the maximum difference in refractive indices (ordinary and extraordinary refractive indices) experienced by radiation with different polarisations within the material.

Birefringent materials are thus capable of splitting a beam of radiation into two beams, each refracted or transmitted at a different angle, and each polarized at a right angle to the other. Certain crystals such as calcite and quartz have this property.

The simplest type of birefringence is that of materials with uniaxial anisotropy. That is, the structure of the material is such that it has an axis of symmetry with all perpendicular directions optically equivalent. This axis is known as the optical axis of the material, and light with linear polarizations parallel and perpendicular to it has unequal indices of refraction; the extraordinary and ordinary indices of refraction (denoted ne, respectively no). The names reflect the fact that, if unpolarized light enters the material at a nonzero acute angle to the optical axis, the component with polarization perpendicular to this axis will be refracted as per the standard law of refraction, while the complementary polarization component will refract at a nonstandard angle determined by the angle of entry and the birefringence. The light will therefore split into two linearly polarized beams, known as ordinary and extraordinary. Exceptions arise when the light propagates either along or orthogonal to the optical axis. In the first case, both polarizations and rays are ordinary and are not split. In the second case also, there is no splitting of the light into two separate directions, but the ordinary and extraordinary components travel at different speeds, and the effect is used to interconvert between linear and circular or elliptical polarizations.

In a biaxial material, there are three refractive indices $\alpha$, $\beta$, and $\gamma$, yet only two rays, which are called the fast and the slow ray. The slow ray is the one for which the material has the highest effective refraction index.

A beam of radiation generally propagates in a beam propagation direction (and accordingly a beam of radiation is often said to have a beam axis parallel to the propagation direction). However, in a beam having such axis radiation in one part of the beam may still propagate in a different direction than radiation of another part of the beam. This is for example the case in a convergent or divergent beam. This is generally not so in e.g. a parallel beam.

The optical axis of an optical system is an imaginary line that defines the path along which light propagates through the system. For a system composed of simple lenses and mirrors, the axis passes through the centre of curvature of each surface, and coincides with the axis of rotational symmetry. The optical axis is often coincident with the system's mechanical axis, but not always, as in the case of off-axis optical systems.

The invention can be applied in an analysis system in which a lateral offset is needed between the location of excitation and the location of detection of the signal/beam caused by the excitation. One such a system is a Spatially Offset Raman Spectroscopy (SORS) system.

The Raman process relies on the inelastic scattering of photons in a material, resulting in an analytical signal at a different wavelength then the excitation wavelength. The energy loss is very specific and contains chemical bond vibrational information that forms a fingerprint of the material.

In order to obtain the fingerprint (Raman spectrum) of a material it is important that the Raman scattered photons can reach the detection system, i.e. photons should originate from a location that is within the numerical aperture of the collection system. In regular Raman spectroscopy excitation and detection therefore occurs on the same location of the material and a signal is detected in backscatter mode usually employing a microscope device. The reader is referred to general description of Raman spectroscopy for more information.

This type of measurement works well for transparent materials, but is usually difficult for materials that are not entirely transparent to the excitation radiation used (light in case of Raman spectroscopy). For those purposes Spatially Offset Raman Spectroscopy (SORS) can be used.

The general principle of a SORS measurement or any other spatial offset measurement (Fluorescence, phosphorescence IR) is explained with reference to FIG. 1.

FIG. 1 shows a sample 101 consisting of two different material layers 102 and 103 on top of each other of which the top layer 102 is only partly transparent to excitation radiation. The excitation radiation is provided by means of beam 104 to the top surface of layer 102 at a location 105 (indicated with 105x on the X-axis that runs parallel to the top surface). The sample is assumed to be rotationally symmetric around the z-axis that runs parallel to beam 104 and a circular excitation spot is assumed. The layer 102 can be seen as a scattering shield made of e.g. a plastic bottle or cardboard box etc.

The excitation radiation travels from the excitation location 105 through the material layers beneath as a consequence of scattering and in doing so excites a volume of material beneath the surface of layer 102. The penetration envelope of excitation radiation changes for increasing depth (compare envelopes 110 and 111 for penetrations 112 and 113, respectively). The excited volume material in turn produces the radiation to be detected (RAMAN Fluorescence Phosphorescence IR etc) which emerges at the surface of layer 102, again through all kinds of scattering processes. The envelope of the emerging detection radiation also changes with depth and resembles the envelopes 110 and 111. Consequently, it turns out that the further away laterally from the excitation location 105 (along the x-axis) one detects the scattered radiation, the greater the relative contribution of the deeper layer to the detection signal is. Hence, e.g. radiation detected at location 106 with spatial offset 107 has a higher relative content of radiation generated by layer 103 than the radiation detected at location 108 with spatial offset 109 that is smaller than spatial offset 107. The opposite holds for the contribution of layer 102 in this case.

The detection of two spectra at two different locations while exciting the sample at the same location and appropriate analysis of these spectra allows separation of the components of a material. In this case since there are only two layers, two measurements suffice to determine the spectra of either one of the layers even without knowing the nature of the shielding partly transparent layer 102. When more layers are involved more measurements may be needed and the data require multivariate analysis to separate the different layers. Note also that one can do such measurements by excitation at one location and measurement at different offset locations or with excitation at different locations while detecting at only one offset detection location. As the result of this analysis is not different from a conventional Raman data analysis, no special data processing is needed accept for multivariate analysis.

The offset in the case of FIG. 1 implies that signal is detected at a position of the sample that is laterally different from the excitation position. Lateral in this case thus means substantially perpendicular to the direction of the excitation beam. As said, the scattering intensity decreases rapidly when a lateral positional difference between excitation and detection is used. Despite this decrease, the signal measured, after certain referencing and compensation largely reflects the 'interior of the' sample instead of the shield. Thus, SO measurement is particularly useful when the data (spectrum) from a scattering surface layer masks most of the data (spectrum) of the material of interest underneath. By applying a spatial offset in the detection path the relative contribution of the data (spectrum) from the material masked by the material on the surface increases offering a unique tool to detect and identify substances hidden from plain sight.

To enable SO measurements in prior art systems, generally a complicated excitation detection apparatus is required usually comprising integrating optics and/or mechanically moving parts such as stages etc. According to the current invention there is provided a spatial offset, single or variable, in a simple way based on different treatment of excitation signal and detection signal based on their polarization. In particular, a spatial difference between the excitation and detection paths in the XY-plane (rather than the XZ or YZ-planes) without changing the optical configuration of a standard backscatter mode system can be made. This idea is based on the recognition of inter alia that scatter processes (such as the Raman scatter) do not have a preferential polarization unless media/material are analysed that have a strong orientation (crystal-lattices, liquid crystals). By providing the excitation radiation in one polarization and selecting the other polarization as the detected radiation from the offset location (both polarizations can be individually selected or set) the spatially offset working mode is achieved.

Any configuration in which a birefringent component is used (in which the birefringence is present in the XY-plane (e.g. perpendicular to the radiation beam transmittance)), will lead to spatial differences between locations of excitation and emission of radiation of a sample. This holds even when randomly polarised radiation impinges on the birefringent component. As indicated earlier, and generally known, such radiation is split into beams with different polarisation by a birefringent component. Therefore any polarisation configuration can be used, as long as the polarisation types are selected such that excitation and emission polarisation directions are orthogonal. This is shown in the table below, which explains the different signals detected in the emission and the selected polarisation direction as a function of the excitation polarisation.

| Excitation polarisation | | Polarization origin for non-offset | | Polarization origin for offset |
|---|---|---|---|---|
| Linear | Horizontal Vertical | Linear | Horizontal Vertical | Vertical Horizontal |
| Circular | Right handed Left handed | Circular | Right handed Left handed | Left handed Right handed |
| Elliptical | Right handing Left handing | Elliptical | Right handing Left handing | Left handing Right handing |

As shown, the non-offset function (unaffected radiation) applies when the polarization is the same as the excitation polarization, whereas the offset function (refraction or deflection of radiation) applies to a different polarization.

Many other combinations of excitation and emission polarisations are possible, such as linearly polarised excitation in, and circularly polarised emission detected. For this instance, a mixed signal will be obtained.

Based on the birefringent properties of materials, it is preferred that the birefringent component (mirror, lens, prism or else) is properly oriented with respect to the plane of incidence of the polarisation and the radiation polarisation direction so as to choose the desired optical function from the birefringent component. In case of a birefringent material this direction should be matched either parallel or perpendicular to the director axis of the birefringent material, as then completely resolved excitation and detection signals can result. In any other situation a mixed state of signal origin will result, not necessarily inhibiting a proper (spatial offset) measurement, but signal origin and ratio of spatial offset versus non-offset signals will become less defined, requiring additional data manipulation to extract the material properties from the data.

The invention can be implemented in multiple arrangements each with its own set of advantages. Each arrangement can be part of an analysis system, permanent or as an accessory to the analysis system.

Figure 2:
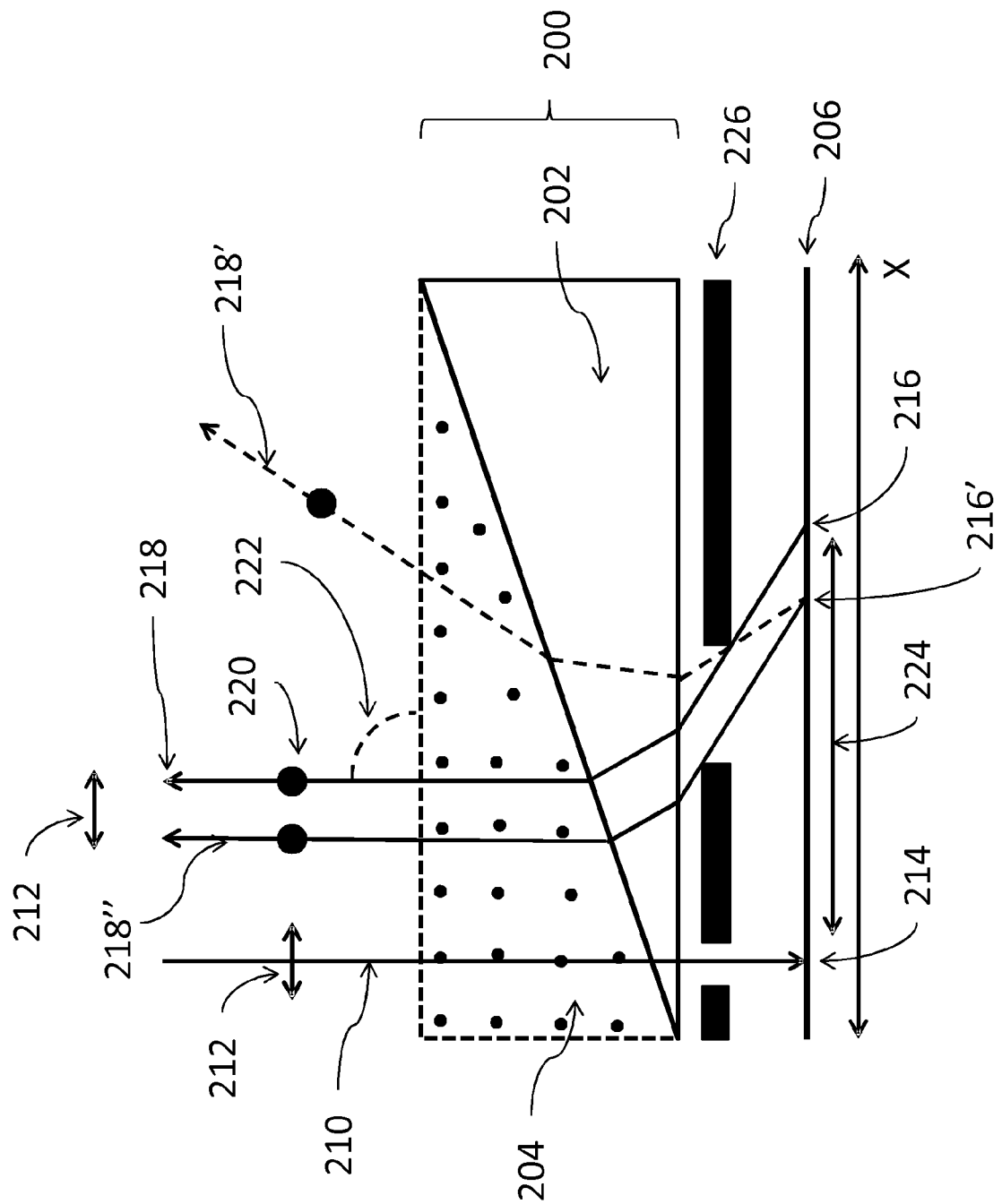
FIG. 2 shows an example arrangement according to the invention comprising a birefringent prism.

A first arrangement comprises at least one birefringent prism. FIG. 2 shows an arrangement with a birefringent prism 200 including an isotropic part 202 and a birefringent part 204. The prism is situated above a surface 206 of a material to be analysed, such as e.g. the surface of layer 102 of FIG. 1.

One of the refractive indices (ordinary ($n_o$) or extraordinary ($n_e$)) of the birefringent part 204 is matched to the refractive index (n) of the isotropic part 202. A beam of excitation radiation e.g. 210 enters the prism at the detection side along a beam propagation axis direction (210) and exits the prism at the excitation side. For the beam 210, which has a polarization (linear in this case, but others are possible) 212 in the plane of drawing, the refractive index of the isotropic part 202 and the ordinary refractive index of the birefringent part 204 are in this example matched and consequently no refraction of this beam occurs. The beam 210 is incident on the surface 206 at location 214 (on the X-axis). The excitation location 214 can correspond e.g to the location of excitation 105 in FIG. 1 (first location). Detection radiation 218 with the correct polarization 220 (i.e. not the same polarization 212 as that of beam 210) emitted within certain angles from the location 216 (second location) by the surface can now be collected by the prism such that it exits the prism at the detection side in the direction opposite to that of the excitation radiation 210, because that detection radiation 218 is refracted by the prism. One such radiation ray is represented by 218 having a polarization 220 perpendicular to polarization 212 (perpendicular to the plane of drawing). For this beam 218, the refractive indices of the parts 202 and 204 of the prism do not match as a consequence of the birefringent nature of part 204, and hence, the beam is deflected, or refracted at the interface between the parts 204 and 202. Note that part 202 will have a refractive index generally different from that of air such that at its boundary a refractive effect will occur for all polarisations. This is however not disturbing the general operating principle of the arrangement.

The angle under which the beam is deflected depends on the three-dimensional orientation of the birefringent surface separating the two parts 202 and 204 and on the difference between the extraordinary refractive index and the ordinary refractive index. The deflection angle can be calculated using standard optics theory based on Snell's law (ni sin θi=nt sin θt) and the appropriate refractive indices.

As an example, consider the beam 218 exiting the prism element at right angles 222. Assume that all materials used have a refractive index of 1.5 (including the ordinary refractive index of the birefringent part 204) and the extraordinary refractive index is 1.75. To create a maximum deflection of 90° it is then necessary that the normal of the refracting surface between part 202 and 204 makes an angle of 41.74° with the exiting beam 218.

The excitation radiation 212 remains un deflected while the detection radiation 218 becomes deflected. The reverse situation where the excitation radiation would be deflected while the detection radiation would be unaffected can equally well be used to create the spatial offset.

The arrangement can thus provide the spatial offset 224 as needed for a SO measurement as explained with reference to FIG. 1 and provide that the excitation radiation beam 212 before entering the prism and the refracted beam 218 after exiting the prism travel along the same axis again just like in a backscatter mode microscope or spectroscopy system. Hence, the arrangement can serve as a simple enhancement for a regular backscatter mode analysis system. The optics or radiation manipulation means of the regular system can be used to provide the beam 212 to the arrangement and for manipulating the detection beam 218 after exiting the arrangement towards the detector of the system. A more complete description of system will be given herein below The arrangement of FIG. 2 can be adjusted to advantage. The ray 218'' indicates that although it comes from a different spatially offset location 216' than the location 216, it is redirected in the same direction as ray 218 and thus when falling in the aperture of the analysis system will be registered by the detector. This may add to reduction of contrast of the device, i.e. in effect one is detecting radiation from all multiple locations on the surface 206 along the X axis, in this case at least from those between location 216 and 216' when allowing a beam defined by 218 and 218'' to reach a detector in one measurement.

The contrast can be increased by defining an aperture at the detection and/or excitation side of the prism 200. This can be a simple pinhole device 226 with adjustable diameter and/or shape if desired with which the beam of detection radiation reaching the detector is defined. The aperture may take any form having such beam limitation function. FIG. 2 shows the aperture 226 at the excitation side of the prism with an opening for the excitation radiation and an opening for the detection radiation. The aperture can also be controllable with respect to lateral position. With such controllability the spatial offset can be determined without loss of contrast.

Sensitivity of the device can also be adjusted. As can be seen from detection radiation ray 218', which can also pass the aperture 226 if present, the amount of rays (number of photons and therewith energy) collected from location 216' is limited as the radiation rays that are emitted from the surface 206 in a different direction than ray 218, are redirected by the arrangement in a direction not parallel to the ray direction 210, which may eventually result in these rays not reaching a detector (the rays are off axis). The numerical aperture (NA) of a complete analysis system will provide the boundaries of this effect.

Figure 3:
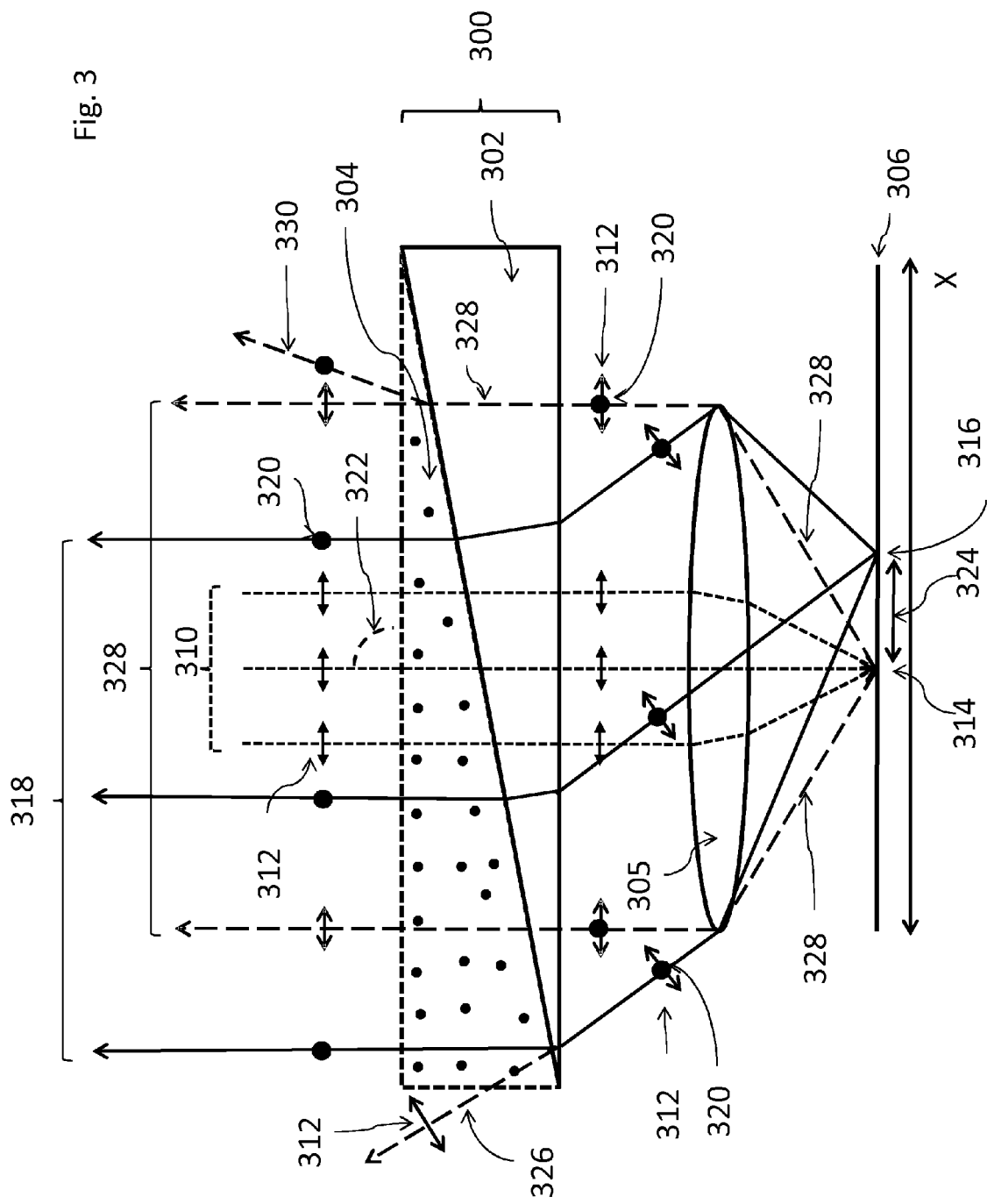
FIG. 3 shows an arrangement according the invention comprising a birefringent prism and a radiation collection lens.

The effect can be reduced by introducing a collection device into the arrangement or the system that collects rays from the surface within a specific cone in which they are emitted from the surface 206. FIG. 3 shows a prism 300 with isotropic part 302 and birefringent part 304. It is the same prism as that of FIG. 2 and it works in the same way. The excitation beam 310 with polarization 312 in the plane of drawing and having a width defined by its outer rays drawn, enters the prism at right angles 322, travels through the prism without being affected and subsequently is focussed by lens 305 onto location 314 of surface 306 of a material to be analysed. The lens 305 functions as a collection device. It collects the entire cone of rays 318 (represented by the solid lines) emitted from location 316 and subsequently redirected by the prism parallel to the direction of the excitation beam 310.

An additional advantage of a collection device in the form of a lens is that contrast is also increased with reference to the situation of FIG. 2. Rays from different location in the X-direction that will be collected within part of the cone of 318 stemming from location 316 is reduced as defined by the aperture (lens opening) of the lens instead of the prism. The pinhole part 226 of FIG. 2 is thus not needed, but may be added as a further improvement for contrast if needed.

FIGS. 4A and 4B show two configurations of an arrangement 400 that can be part of a detection system and that incorporates the arrangement of FIG. 3. This simple system can be and regularly is part of a conventional microscope system as used in numerous Fluorescence and/or Raman spectrometers. Features that represent the same features as described with regard to the arrangement of FIG. 3 have been given the same reference numerals.

In the arrangement or system there is the prism 300 with the isotropic part 302 and the birefringent part 304 and there is the lens 305 placed at the excitation side of the prism. The prism 300 and lens 305 operate as described with ref. to FIG. 3. In the arrangement there is a notch or edge filter 402 (as a beam splitter) that redirects the excitation beam 310 from a radiation source (not shown) with polarization direction 312 in the plane of drawing towards the prism such that it enters the prism at right angles. The beam traverses the prism unaffected and is incident on the sample surface 306 at location 314 after having been focussed by the lens 305 just as described with reference to FIG. 3. The notch or edge filter functions as a wavelength-selective reflector or beam splitter, substantially reflecting the excitation beam 310.

Detection radiation with polarization 320 is collected by the lens (polarizations 312 and 320 are collected together) from location 316 and the part with polarization 320 is redirected by the prism as beam 318 as described with reference to FIG. 3 towards the notch or the edge filter 402. This beam 318 will pass the filter due to the fact that it is shifted in wavelength caused by the excitation process in the sample (Raman or other such as fluorescence or phosphorescence). The filter device 404 (which can be for example a polarizer or analyzer) is adjusted such that it passes the beam 318 to the detector 406. Note that part of the detection radiation with polarization 312 that was also collected by the lens 305, is not redirected by the prism 300 as it has the wrong polarization for that and thus leaves the prism in its collection direction 326, i.e off axis (This is only indicated in FIG. 3 for one ray with polarization 312 of beam 318). Therefore, it will not reach the detector 404.

The backscattered radiation beam 318 coming from the excitation location 314 caused by excitation at that spot is also collected by the lens 305. Any excitation radiation therein, irrespective of its polarization, that reaches the notch or edge filter 402 will be redirected by this edge or notch filter out of the path leading towards 404. Furthermore, the detection radiation part of this beam 328 originating from location 314, and thus shifted in wavelength, which has the polarization 320 will be redirected by the prism 300 off axis as a beam with direction that is the same as ray 330 (see FIG. 3) so that it will not reach the detector. However, the part of the detection radiation of beam 328 with the polarization 312 is passed by the prism 302 unaffected in the direction of the detector. It will pass the filter 402, but is prevented from reaching the detector by the selection device 404 due to it having the wrong polarization.

Detection radiation relating to the location 316 can thus be recorded from the beam 318, without interference of radiation from other sample location.

For the SO method, one may also need the data of at least one other location (if this is not already known from another reference) to be able to deduce the radiation that is specifically originating from one layer (e.g. the non-surface layer) of a two layer sample (see description of general operation of SO measurement with regard to FIG. 1). More such different locations are needed when the sample is more complex such as having multiple layers etc. The reader is referred to further background reading on SORS measurement principles and data treatment using multivariate analysis.

FIGS. 5A and 5B show a prism 500, which is an alternative configuration of a prism of FIGS. 2 and 3, from the side and top, respectively. It will operate as the one of FIG. 2 or 3, but allows the design to be different. The prism is built up from multiple smaller sub-prisms 501 placed alongside each other. Each of the sub-prisms 501 has an isotropic part 502 and the anisotropic birefringent part 504. A flatter prism may be achieved for refracting surface between parts 502 and 504 having the same angle over the width of the whole prism when compared to the prisms of FIGS. 2 and 3. FIG. 5B shows the parallel orientation of the birefringent material molecule orientation with the solid small stripes each representing the director of a birefringent material molecule.

In the implementation with the prism as described herein before, the directional control of the excitation signal relative to the emission signal within a Spatially Offset system is used such that spot or line excitation and/or detection is used. These configurations are not always the most efficient way to use an offset between excitation and detection.

Other shapes or cross-sections of excitation and detection areas with offset can be used to advantage. One alternative and preferred arrangement is based on providing ring excitation and/or detection. In the ring excitation method many points are excited at the same distance from the centre of the ring, from which the signal can be collected. This provides a lower detection limit and/or reduced measurement time. A further advantage of this configuration is that a higher excitation radiation power can be used without the risk of damaging the material, as the flux of the signal at the excitation surface is lower when the excitation area increases. Alternatively, with the arrangement in reverse mode, collection of emission is possible from a ring around an excitation point. Especially when large offsets are used (corresponding to greater depth measurement in the turbid media), these configurations give improved efficiency compared to point excitation and point collection.

FIG. 6 represents a surface 600 of a sample viewed from the top. On the surface is shown a location in the form of a central spot 602 and a surrounding ring 604. The spot can be the location where excitation radiation is provided to the surface and the ring can be where the emission radiation is collected, or else the ring can be the excitation signal and the emission can be collected from the central spot. The spatial offset is given by the distance 606.

Figure 7:
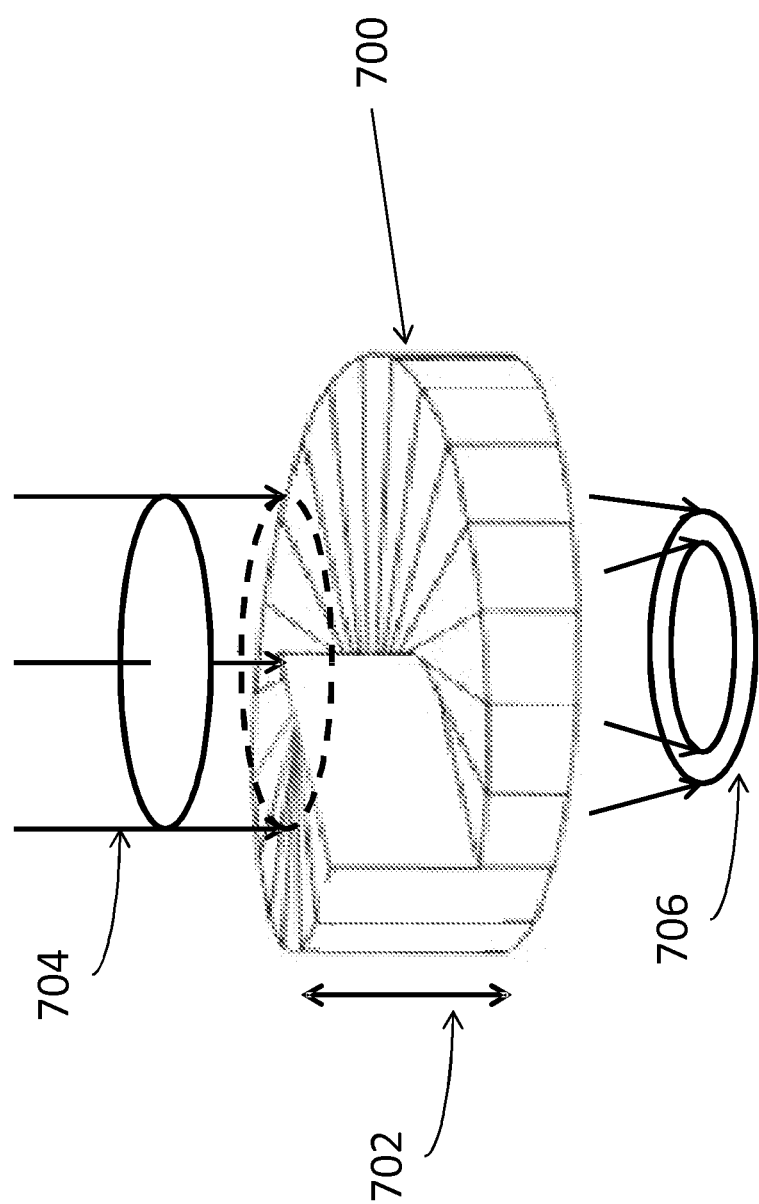
FIG. 7 shows a spiral plate and how it can be used to obtain the excitation and collection pattern of FIG. 6.

FIG. 7 shows an arrangement with which such ring excitation/detection can be achieved. Part 700 represents a spiral plate, which can be used to provide generation of a ring of illumination with a spatial offset compared to the detection point in the center of the ring. The spiral plate has a thickness 702 which varies circumferentially around the plate, but is uniform radially. The plate is made of a material that is substantially transparent to excitation and detection radiation. The spiral plate functions therewith as a polarization sensitive beam deflector in the form of a circular prism. As a consequence, the spiral plate converts a central beam 704 into a beam 706 which has a ring shaped cross section.

A description of phase plate elements (although non-birefringent) is found in reference "Half integral spiral phase plates for optical wavelengths", J. Opt. A: Pure appl. Opt. 6 (2004) S288-S290. A further description is provided in "Production and characterization of spiral phase plates for optical wavelengths", Appl. Opt. 43, 688-694 (2004). These spiral plates can be used for the invention even when they are isotropic. Either the plate is then made of birefringent material, or it is made of isotropic material and then forms the prismatic surfaces by contacting birefringent material at its stepped side. As long as the birefringent spiral plate is capable of refracting one polarization, while leaving the other one unaffected, it can be used in the invention to create the offset between excitation and detection location.

An example of a possible manufacturing process of a birefringent spiral plate is described according to steps explained with reference to FIGS. 8A to 8D. FIG. 8A shows a spiral plate 800 (same as that of FIG. 7) on top of a substrate 802. This can be made by starting with a diamond turned mold, for example in brass. From this mold, a replica is made via photo-replication, as described in "Production and characterization of spiral phase plates for optical wavelengths", Appl. Opt. 43, 688-694 (2004), also referenced above. The result of this photo-replication process is a replica of the mold on top of a substrate in the form of the spiral plate 700. The spiral phase plate can be and preferably is made of an isotropic transparent plastic material.

Next an alignment layer is provided on top of the structure via e.g. spin-coating from solution. An alignment layer is also provided on a second substrate 804. The alignment layers are rubbed in the directions 808 and 810, preferably parallel to the height step direction of the spiral phase plate. This also minimizes artifacts at the highest step interface of the spiral as the molecules are oriented parallel to that step interface surface also. The substrates can for example be glass slides or transparent plastic substrates.

Spacing elements 812 and 814 are then provided, which are sufficiently thick to accommodate the replicated spiral phase plate 800, and the two substrates and spacers are brought together as shown in FIG. 8C. The spacers and substrates can for example be glued together.

The cavity formed as such is then filled with a suitable birefringent material 816 which may be a Liquid Crystal as indicated with the ensemble of parallel lines representing liquid crystal molecules in FIG. 8D. The liquid crystal material molecules will align according to the rubbing direction of the alignment layer on the substrates.

The element is closed for example from the front and back with a droplet of suitable material, such as Norland 65 UV curable glue (not shown for clarity in FIG. 8D). Other means of closure can be used as well.

The liquid crystal may be UV cured if such material is used. Reactive Mesogens e.g. sold by Merck can be employed for that purpose. In that way a solid birefringent material can be obtained that nicely encloses the spiral phase plate structure. Alternatively, the liquid crystal material can be kept as is, e.g. for purposes of making a switchable or adjustable device.

The above process can be used to manufacture all types of replica based (solid material that defines a deflection or refraction surface of a device (prisms and lens) structures as described herein below.

Just like with the prism arrangement, the birefringent material and spiral plate material are chosen such that at least one of the ordinary and extraordinary refractive indices of the birefringent material is matched with a refractive index of the spiral plate material while the other one is not. In this case the material of the spiral plate structure is isotropic having one single index of refraction. Hence, at the interface between the surface of the spiral plate and the birefringent material, there is a refractive index difference for radiation with one polarization, while there is no such difference for radiation with another polarization.

The operation of the arrangement to create the offset between two differently polarized radiation beams is then largely comparable to that of the prism. Thus, light with one linear polarization is not affected by any refractive index change in the arrangement, while the other linear polarization is refracted due to the refractive index difference at the interface. Hence, an excitation beam with the correct polarization can travel straight through the arrangement while radiation collected from the circle and of different polarization than the excitation radiation is refracted in the correct direction again for a backscatter mode operating analysis system.

Figure 9:
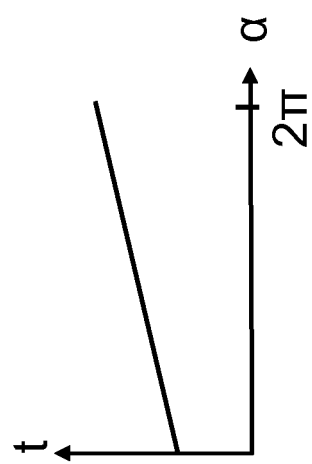
FIGS. 9A and 9B show how the shape of the spiral plate can be varied to change the excitation and collection pattern.
Figure 9:
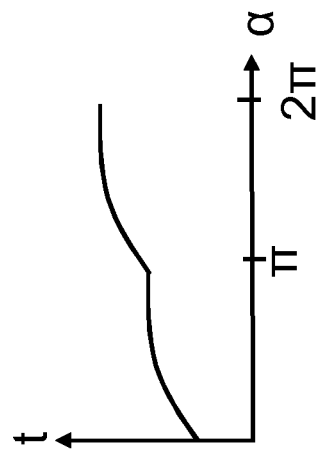

In the example, the spiral plate has a smooth and uniform increase in thickness around the azimuth angle. This uniform increase in thickness with respect to azimuth angle gives a circular illumination pattern. However, if a non-uniform increase in thickness is used, the illumination shape can be changed, for example to an ellipse. Thus, by varying the solid body shape as a function of azimuth angle, the illumination pattern shape can be changed. For example, FIG. 9A shows how a linear increase of the body thickness (t) as function of azimuth angle ($\alpha$) creates a circular illumination pattern, where the diameter of the circular pattern is altered by using a different slope. Offset is related to this circle diameter and hence, a variable offset option can be provided by using a plurality of interchangeable arrangements, each one providing a different circular illumination pattern of the same shape. Alternatively, or additionally, the shapes can be varied for each of the arrangements.

Shapes of the output pattern of a spiral phase plate can be changed by changing the linear thickness increase with circumference to another function. For example, FIG. 9B shows the body thickness as function of angle to create an elliptical illumination pattern.

Instead of creating a ring beam, another example is to create several points of excitation and a single point of detection or vice versa. Using structural features in a birefringent material (such as e.g. a liquid crystal material), an element can be made that holographically produces several points and/or illumination shapes, while a signal is collected from a single spot. The advantage of this configuration is that highly specific illumination of non-flat surfaces is possible. Likewise, it allows the use of multiplexing or the use of higher laser power for excitation without the risk of damaging the material. In this way, diffractive optical elements can be used to generate a desired set of excitation points. Circular elements can be used to generate patterns achieving the same advantages.

Another way to implement the invention relates to a difference between the locations of excitation and detection in the depth direction (z-direction of a sample running from outside to inside of sample usually perpendicular to surface of the sample). This can be achieved with an arrangement that provides a difference of depth to which an excitation beam is focussed and a focal point from which emitted light is collected. In case non transparent media are analysed with such system the surface of the medium to be analysed makes different cross sectional areas with the excitation radiation beam and detection radiation beam. For example, the excitation beam may be focussed at the surface, and the focus of a detection beam can be inside the medium (behind the surface) such that the area of which detection radiation is collected by the arrangement is larger than the focus of the excitation area.

Figure 10:
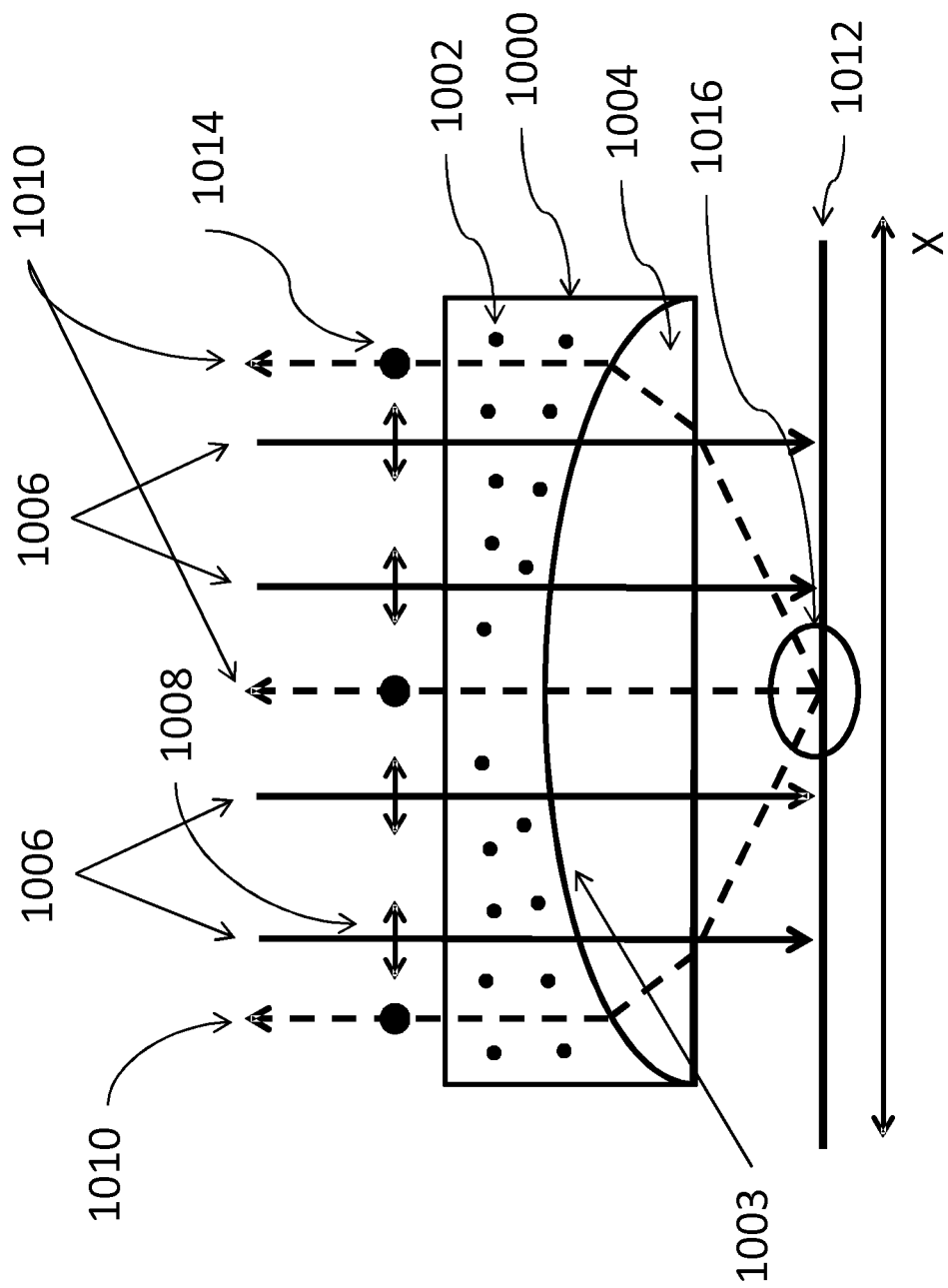
FIG. 10 shows an example arrangement according to the invention comprising a birefringent lens.

A first example arrangement is based on the use of optical elements as is shown in FIG. 10. The arrangement comprises a birefringent lens 1000 that includes a birefringent part 1002 having an ordinary refractive index ($n_o$) that is different from its extraordinary refractive index ($n_e$) and an isotropic part 1004 with a single isotropic refractive index (n). The parts 1002 and 1004 define a curved (lens) surface 1003 between them. One of the ordinary and extraordinary indices of refraction of part 1002 is matched with the isotropic index of refraction of part 1004 so that consequently the other one is not. In this case, the parts are chosen such that the non-matching indexes of refraction form a converging lens. However, other matching may be chosen as described herein below. In the case of FIG. 10, the indexes of refraction are such that the excitation radiation beam 1006 with linear polarization 1008 in the plane of drawing, is unaffected by the arrangement due to it responding to the matched indices of refraction at the surface 1003.

As described for the prism examples, linearly polarised emitted radiation 1010, for example Raman scattering or fluorescence caused by the excitation beam 1006 in a sample with the surface 1012, may have a radiation fraction with a linear polarisation vector 1014 perpendicular to that of excitation radiation 1006. This detected radiation with polarisation 1014 responds to the lens surface 1003 based on the different refractive indices of parts 1002 and 1004 and hence is refracted and collected by the arrangement as if it were originating from a focal point 1016. This means that while the excitation radiation 1006 passes the lens unrefracted to excite a relatively large material volume behind the lens, the emitted radiation is only collected by the lens from a specific focal point 1016.

The above situation of excitation/collection can be reversed using the same lens as shown in FIG. 10 where the excitation radiation 1006 is exchanged for the emitted and collected radiation so that the excitation radiation is focussed to the point 1016, and the detected/emitted radiation 1010, is unaffected. Thus, with the arrangement substantial decoupling of excitation and emission radiation can be achieved through independent directional control of the excitation and emission radiation with respect to each other based on polarization.

The final focal length of the lens depends on the difference in refractive index observed on both sides of the refractive surface 1003 as well as on the curvature of the lens surface. For a birefringent lens the refractive index experienced by the light passing through it, depends on the orientation of the polarization of the light with respect to the director (main orientation axis) of the birefringent material. A difference is made between the ordinary and extraordinary refractive index. In principle with the assumption of a spherical lens, the focal depth can be calculated using $f=R/\Delta n$, in which f is the focal length, R is the radius of curvature of the lens, and $\Delta n$ is the difference in refractive index at the interface between the materials facing each other. The reader is referred to standard optical theory for definition of birefringence and related commonly known optical terminology. See for example Hecht, Optics 3rd edition 1998 published by Addison Wesley Longman, Inc.

Figure 11A:
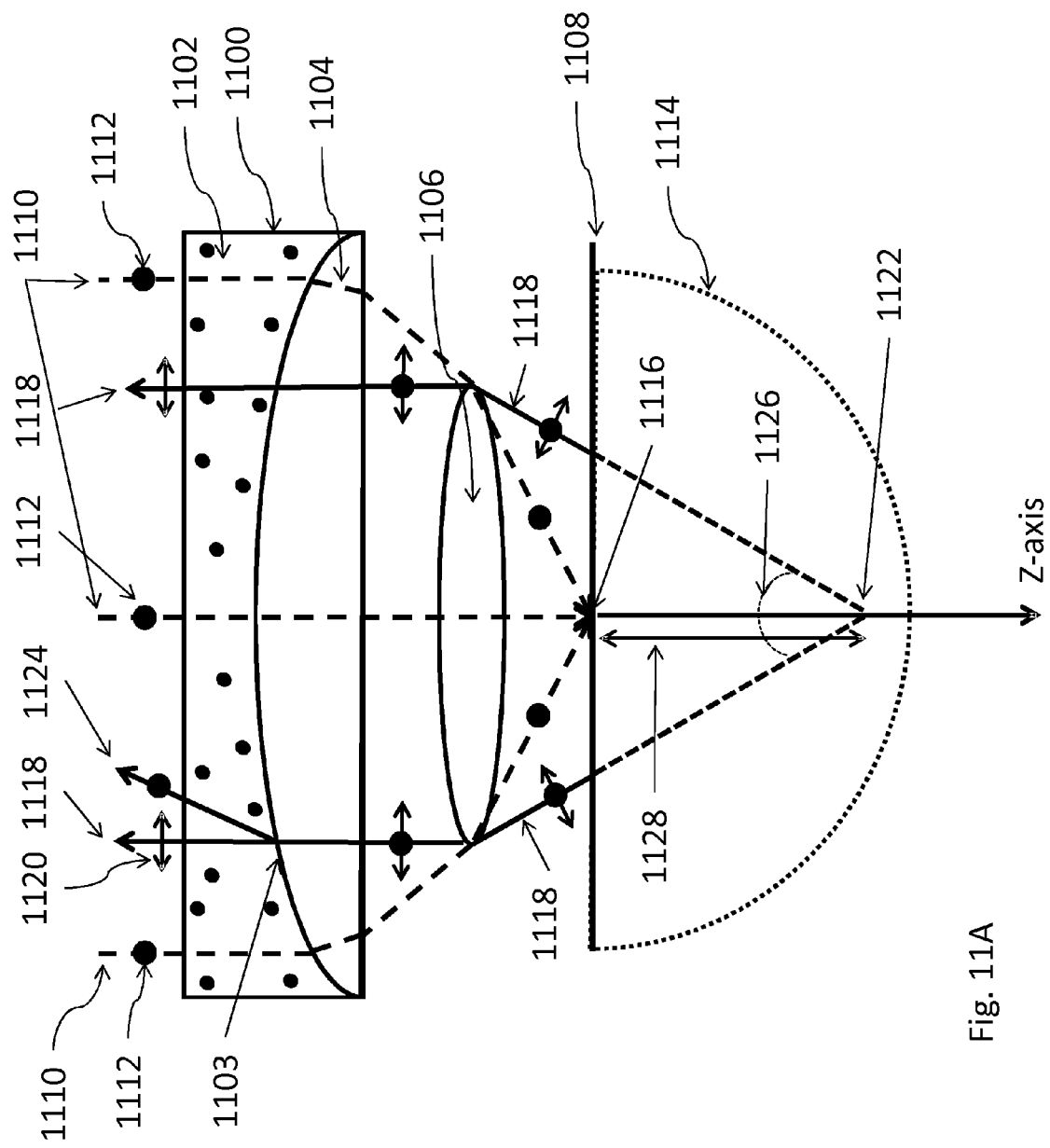
FIGS. 11A and 11B show an example arrangement according to the invention comprising a birefringent lens and a radiation collection lens (objective).
Figure 11B:
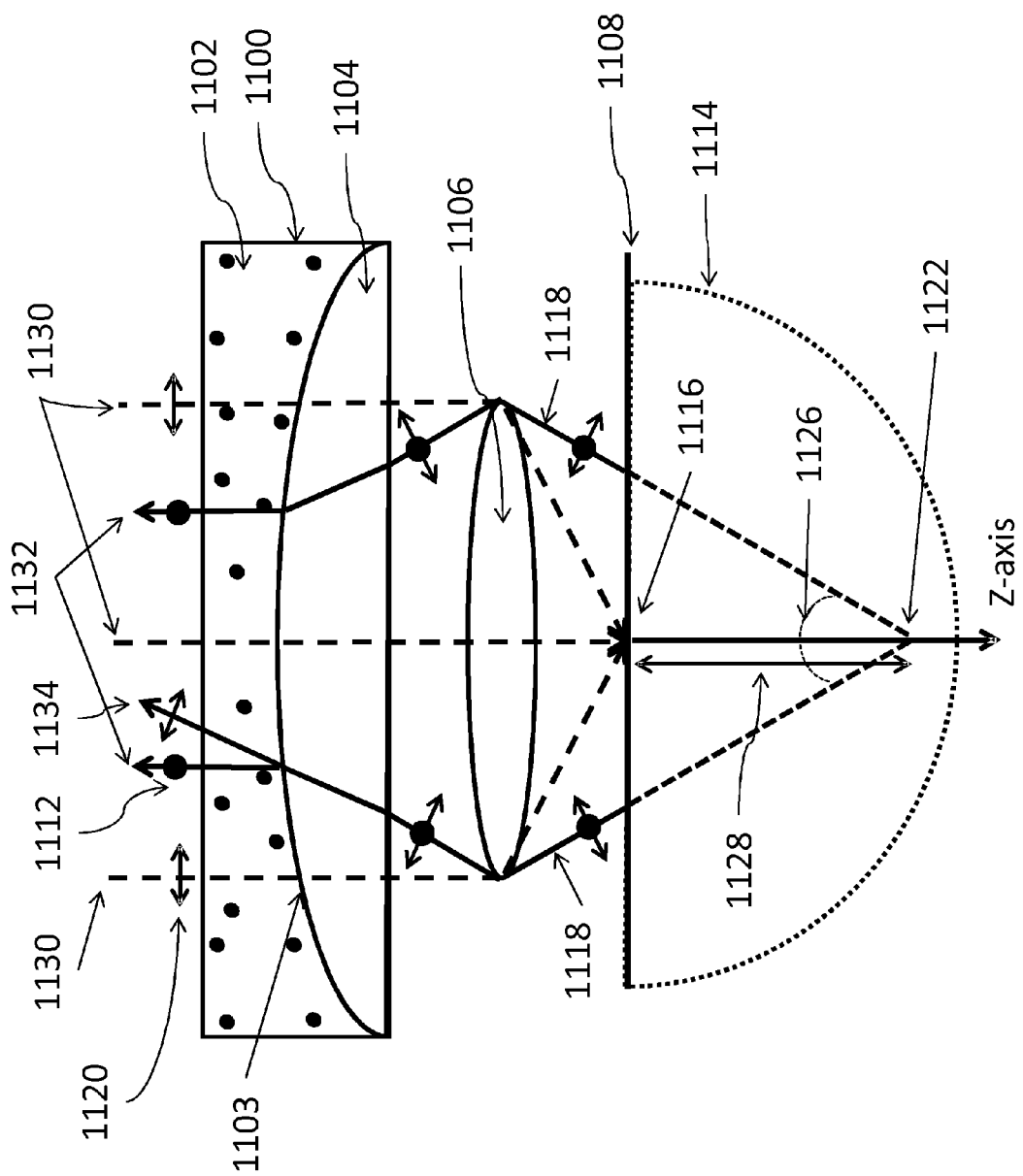

The birefringent lens can be used in an arrangement, or systems as schematically described with reference to FIGS. 4A and 4B by replacing the birefringent prism for the birefringent lens. The described advantages of other features of the arrangement of FIGS. 4A and 4B, such as e.g. filters, collection lenses etc equally apply to the arrangement having the lens. In FIGS. 11A and 11B two examples arrangements including the birefringent lens and collection lenses are shown that provide a parallel beam of detection radiation as may be used in the arrangement or system of FIGS. 4A and 4B. The arrangement of FIG. 11A provides adjustable focal depth for excitation radiation while leaving detection radiation focus depth in the material unaltered. In contrast, the arrangement of FIG. 11B provides a single focal depth while detection focus depth can be altered.

In Both FIGS. 11A and 11B, the arrangement includes the birefringent lens 1100 with isotropic part 1104 and birefringent part 1102 and a surface 1103 defined in between. There is a collector lens 1106 of isotropic material placed in between the part 1100 and a sample with surface 1108. The sample may be, and in this case is, at least partly non-transparent for the excitation and detection radiation. In the arrangement of FIG. 11A the refractive indices of the parts 1102 and 1104 are chosen such that a converging lens results for radiation that has the correct linear polarisation while no lens function is generated for the orthogonal polarisation. In FIG. 11B, the refractive indices of the parts 1102 and 1104 are chosen such that a diverging lens results for radiation that has the correct linear polarisation while no lens function is generated for the orthogonal polarisation.

With the arrangement of FIG. 11A, a beam of excitation radiation 1110 having linear polarisation 1112 is refracted by the birefringent lens 1100 and subsequently focussed by the lens 1106 on the sample surface 1108 in the focal point 1116. The lens strength of the part 1100 determines the depth (along the Z-axis) of the focus.

The excitation protrudes in the material with a volume defined by the boundary 1114, causing detection radiation that after internal scattering eventually may leave the surface 1108 of the partially transparent sample. A part of the detection radiation that leaves the surface 1108 is collected by the lens 1106 and converged into a parallel beam before it is sent to the birefringent part 1100. More specifically, detection radiation that leaves the surface 1108 in a direction as if it originated from an imaginary focal point positioned on the Z axis (depth direction of the material) in between the focal point of excitation 1116 and the imaginary focal point 1122 can be collected in this way. In FIG. 11A the maximum cone of radiation collected is defined by the imaginary focal point 1122 and an azimuth angle 1126, as then light exiting the surface 1108 within this cone exactly fills the entire collection lens aperture and ends up in the parallel converged beam. Congruent cones of light are collected from focal points with smaller Z value (smaller depth 1128 in the material). Hence radiation collected in this way stems from the material below the point 1116 and to a lesser extent even below point 1122 due to the internal scattering of radiation.

In the arrangement of FIG. 11B the excitation radiation 1130 with polarization 1132 in the plane of drawing is left unaltered by the birefringent part 1100, to be focussed by the lens 1106 on the sample surface 1108 in the focal point 1116. This creates excitation of the sample in a volume bound by the boundary 1114.

The detection radiation created by the excitation can be collected by the lens 1106 in much the same way as with arrangement 11A. The difference is only that in the arrangement of FIG. 11B, it is the part of the detection radiation with polarization 1112 that is redirected into a parallel beam and sent to the detector. Hence with this configuration the collection focal depth 1122 can be varied with the strength of the lens 1100 while not affecting the focal point 1116. Note that again the detection radiation 1134 with polarization 1120 is not refracted by the part 1100 and thus will not reach the detector. The Collection lens may be circular for spot excitation and collection, or may be cylindrical for line excitation and collection. Other shapes can be used to tune the shape of the spot for excitation and or detection.

In much the same way as described with reference to FIG. 1, the excitation of a sample with the lens arrangement at point 1116 (corresponding to point 105) causes that around the excitation point at the surface the envelope of detection signal stemming from different depth within the sample changes with distance from the excitation point. The collection device, in this case a lens 1106, is placed at the radiation excitation side of the prisms or lens examples described hereinabove.

Again a collection device may be placed without loss of effect at the radiation detection side (in between birefringent component and a detector). It is however preferred to have it at the excitation side. In this case regular objectives of a microscope could be used as part of the arrangement attached to the objective position of a microscope.

The birefringent components such as e.g. the prism or lens are accompanied with a number of design rules. In principle, the typical dimensions such as the diameter of the birefringent component are often matched or slightly larger than the beam diameter passing the system (hence adjusted to e.g. microscope).

As described hereinbefore, it is possible to use the component solely, in which the birefringent component acts as the main refractive element and possibly also as collection element if it is includes a lens. The birefringent component can however be combined with a conventional microscope objective as the collection device and other parts of microscopes forming parts of the arrangement as described with ref. to FIGS. 4A and 4B. Having a separate collection lens has the advantage that the lens strength of the arrangement will not be solely determined by the power of the birefringent component. As a result influences of aberrations, especially astigmatism, can be largely suppressed.

Solid state birefringent materials can be used for the birefringent parts of the invention. The isotropic part of all birefringent elements in the arrangements can in principle be absent. The surrounding then can function as isotropic part. If the isotropic index of refraction does not match any of the refractive indices of the birefringent material then both polarisation will be refracted, albeit still in a different way thus suitable for creating the offset. Alternatively, the surroundings of the birefringent part already have an index that substantially matches one of the ordinary and extraordinary refractive indices of the birefringent material by choosing a suitable birefringent material with respect to its surroundings (surroundings such as air, nitrogen or even liquids can be chosen). Thus, one can use birefringent crystals or parts that are polished into a certain optical shape (mirror, prism, spiral plate or lens), with or without an isotropic part. Examples of such materials are calcite and lithiumniobate. For example calcite is used in a Glan-Thompson prism which is used to separate unpolarised light into two individual linear polarisation components.

The birefringent parts can also be made using organic birefringent materials such as Liquid Crystalline (LC) materials either in their pristine form (as liquid crystal material), or in polymerised form with birefringence fixed by the polymerisation. A typical Liquid crystal material that could be used is BL009 ($\Delta n=0.281$, $n_e=1.810$), obtainable from Merck Darmstadt, a nematic liquid crystal. Given the high birefringence of this specific liquid crystal (usually quantified as the difference between $n_e$ and $n_o$) the radius of a birefringent component refractive lens surface or the angle of the prismatic surface can be limited leading to a small height or thickness of the birefringent component. If an adjustable component (see herein below) is made of switchable material (non solidified liquid crystal), faster switching speeds result for thinner liquid crystal layers.

If used in pristine form, a liquid crystal orientation layer such as polyimide is provided over a replica surface having the shape of the birefringent surface before bringing the surface in contact with a liquid crystal. A further transparent part may be used to enclose the liquid crystal containing gap in between the replica surface and a further surface of the transparent part. Alternatively, for Graded index devices, the liquid crystal in pristine form can be contained between two parallel flat transparent parts at least one of which has the necessary electrodes and at least one of which has the polyimide alignment layers. The person skilled in the art will know how to orient liquid crystal layers. The anisotropic part (replica part) of a birefringent component can be made of a transparent organic polymer material using photo replication. Materials that can be used for the replicas include: solid state crystals, polyehtyleneterephtalate (PET) and Polyehtylene naphtalate (PEN) foils stretched in one direction and subsequently embossed to provide the refractive surfaces may be used as replica structures for the birefringent component.

Solid state organic polymer birefringent lenses (described as in sheet form) used for other purposes such as 3D tv or optical disc, and their manufacturing procedures are known in the art (refer to WO2004059629, WO2004059627).

The radiation processing parts of the invention will be designed according to the frequency of electromagnetic radiation used. Although the invention is of particular interest for systems using a visible light source such as a laser or diode, which make use of optical components, the invention can be applied to arrangements and systems operating in the electromagnetic spectrum generally (i.e. including microwave, terahertz, infrared, near infrared, visible and ultraviolet, x-ray and gamma spectroscopy). It is within the scope of the invention that components are included that comprise materials that are at least partially (rather than fully) transmissive to the radiation source. Furthermore it is of particular interest to use materials that have different refractive properties for different polarisation directions at the used excitation wavelength. As a result, organic materials such as liquid crystals are mainly used with the ultraviolet up till near infrared region of the electromagnetic spectrum. Note however that these materials can also be used within the microwave and terahertz range. An example of a liquid crystal used in these ranges is an isothiocyanate.

Usually, liquid crystals can be used within only very small bands in the infrared wavelength range impeding the use of these materials here. Therefore inorganic crystals, such as Calcite (Calcium carbonate) and more explicitly Cadmium sulfide and Cadmium selenide are more appropriate for infrared based arrangements and systems.

A birefringent component as described herein above, can be used in analysis devices such as microscopes, luminescence (fluorescence and/or phosphorescence) based microscopes, or RAMAN measurement devices.

A birefringent component can be based on the combination of two birefringent materials facing each other (rather than a switchable birefringent material combined with an isotropic material). This can give improved performance in terms of rays that pass the component off axis due to better matching of refractive indices for those off axis rays.

Even when the material is not transparent, since excitation light is transported over larger distances prior to reaching the location of emission location dependent compositional information can be obtained with the SO methods. In other words, the path along which information is collected from the sample is determined not only by the individual locations of excitation and emission but along the entire path between and to a lesser extent beyond these locations as excitation is performed along the entire track.

It is thus advantageous to have an arrangement and analysis system including such arrangement that can detect simultaneously or sequentially at different spatial offset in an easy way. By exciting at different positions on a sample while keeping the emission/detection position constant, or vice versa, information is obtained that with the help of e.g. multivariate analysis can provide compositional data of the material as a function of location in the sample, even if the surface of the sample is largely or not entirely transparent.

In principle variable offset is available with any of the implementations given above, as with a simple selection of polarisation for the detection radiation, radiation can be detected either directly from the excitation point (first location), or from a spatially offset location (second location). This selection has been described with reference to FIGS. 4A and 4B and can e.g. be done with the polarisation selector 404.

However, to implement even more advanced variable spatial offset measurements, multiple other options exist.

The arrangement can include at least two birefringent parts each one providing a different spatial offset. The multiple birefringent parts can be e.g. multiple prisms, multiple spiral plates and/or multiple lenses. Combinations can be used as well. Two or more birefringent parts (such as the prisms and/or lenses) can be placed in series in the radiation path or can be used sequentially, in parallel. The arrangement preferably is then designed such that the different birefringent parts are interchangeable or replaceable, either by hand or mechanically and preferably even electrically driven using motors or the like. For an analysis system that needs to operate at more than one focus depth within a sample material, the arrangement can comprise a plurality of such lenses. Lenses may be the same or, each of them may have different optical strength associated with it.

Thus, one can make use of a series of prisms, a series of lenses or a series of other components that provide the same type of manipulation, but to a different extent. Thus in the series of prisms the angle of the deflection surface can be varied such that the spatial offset is different for different prisms. One can then replace prisms (or add them in series) to increase the spatial offset without affecting excitation location. The same can be done with birefringent lenses with different strength. No adjustment of sample with respect to component should be necessary to do the consecutive measurements.

To this end the arrangement can have a holder for holding such a series of birefringent component. The arrangement can have a sliding or rotator device to accommodate the birefringent parts and to be able to slide or rotate to change birefringent part in the radiation path of the arrangement or analysis system using the sliding or rotation operation. There may be even more than one of such sliders and rotators in parallel allowing individual choice of birefringent parts in series in the light path.

Alternatively, and preferably an arrangement and system with tuneable spatial offset (tuneable deflection or tuneable convergence, divergence or depth of focus) offset is used, preferably such that this tuneable function is provided by using an electrically driven part without having movable parts. This arrangement then provides a controlled depth of focus or spatial offset without having mechanical moving parts in the arrangement. Multiple options to implement such function exist.

Figure 13A:
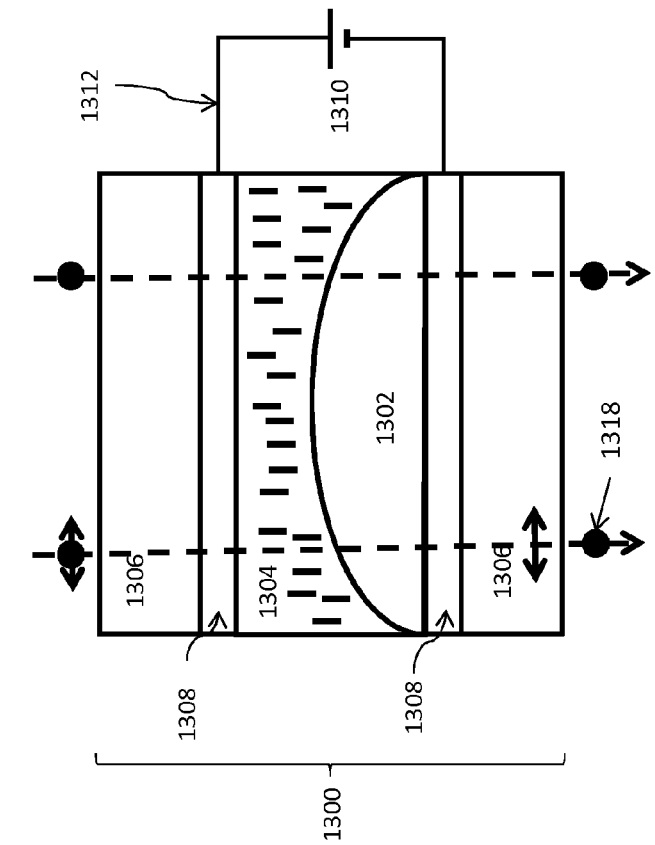
FIGS. 13A and 13B show a birefringent lens with adjustable birefringence based on a liquid crystal layer and replica layer and how it's birefringence can provide different operating modes.
Figure 13B:
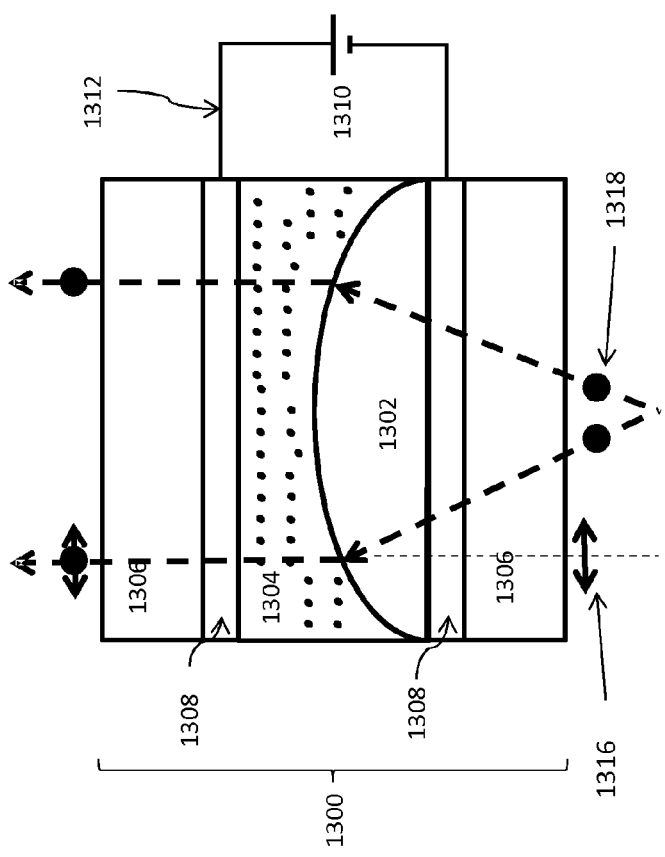

A first preferred option makes use of electrically driven liquid crystal based birefringent parts. FIGS. 12A and 12B show a liquid crystal based birefringent prism. FIGS. 13A and 13B show a liquid crystal based lens with replica layer and FIGS. 13C and 13D. show a liquid crystal based GRaded INdex (GRIN) lens. Each of these devices can be adjusted by application of a voltage signal applied to electrodes.

In these devices (liquid crystal based birefringent parts) only one linear polarization is influenced by electrical adjustment and the other polarization remains unaltered during electrical adjustment. Hence this results in a variable spatial difference between excitation and detection location as a function of electrical driving in all such devices.

The electrically adjustable birefringent prism of FIG. 12 includes the isotropic solid material parts 1202 situated on a glass plate 1206 with in between a sheet like electrode 1208. In this case that is a transparent Indium Tin Oxide (ITO) electrode covered glass plate. The parts 1202 are covered with an alignment layer rubbed in the direction perpendicular to the plane of drawing. On top of the alignment layer is a liquid crystal material layer 1204 defining the prism surface together with the parts 1202. The device is covered by an additional glass plate 1206 having another ITO sheet like electrode 1208 and a second alignment layer (with alignment perpendicular to the plane of drawing) in between the electrode and the liquid crystal material 1204. The alignment layers take care of the ordering of the liquid crystal molecules with their directors (dipole moments) parallel to the direction perpendicular to the plane of drawing (directors indicated with the dots in layer 1204). In practice this is a liquid crystal filled cell having spacers at the side (not drawn) to contain the liquid crystal in the cell. The electrodes are electrically connected using wiring 1212 to a voltage source 1210 that is adjustable.

By means of the electrodes the voltage over the liquid crystal cell may be adjusted. At zero voltage in FIG. 12A, the liquid crystal molecules are aligned perpendicular to the plane of drawing (and a birefringent prism is defined that can be used as indicated with regard to FIGS. 2 to 4 herein above). Hence, radiation with polarisation 1218 collected under an angle 1214 is refracted (deflected) while radiation collected with polarisation 1216 is unaffected by the prism (for polarisation 1216 there is refractive index matching between 1204 and 1202).

To adjust the strength of the prism, the voltage can be raised such that the liquid crystal molecules reorient to a certain extent, i.e. more parallel to the electrical field lines. In the ultimate reorientation they will orient completely parallel to the field lines as drawn in FIG. 12B. The reorientation causes the effective refractive index of the birefringent liquid crystal material to change (as its optical axis has reoriented with respect to the incoming radiation) has changed and therewith the refractive power of the prism is altered which determines the angle 1214 under which the radiation 1218 can be collected in order to refract it parallel to radiation of polarization 1216. Hence, the voltage determines the offset of the arrangement.

In the ultimate state of FIG. 12B, the voltage is such that all liquid crystal molecules are aligned parallel to the electrical field lines, i.e. parallel to the plane of drawing and the refractive index difference between 1204 and 1202 disappears altogether for all refractive indices, such that the device then functions as a transparent plate for radiation with polarisation 1216 and 1218. This can serve as the off state of the adjustable device and arrangement having such a device.

Note that for Liquid Crystal Cell based components, both AC and DC voltage driving may be applied for adjustment or switching of the component. However, AC driving is often preferred to reduce the effect of polarisation of the liquid crystal cell due to the presence of dipolar and/or ionic materials in such cells.

The same liquid crystal tuning principles may be used in the liquid crystal spiral plate or the lenses.

Figure 8:
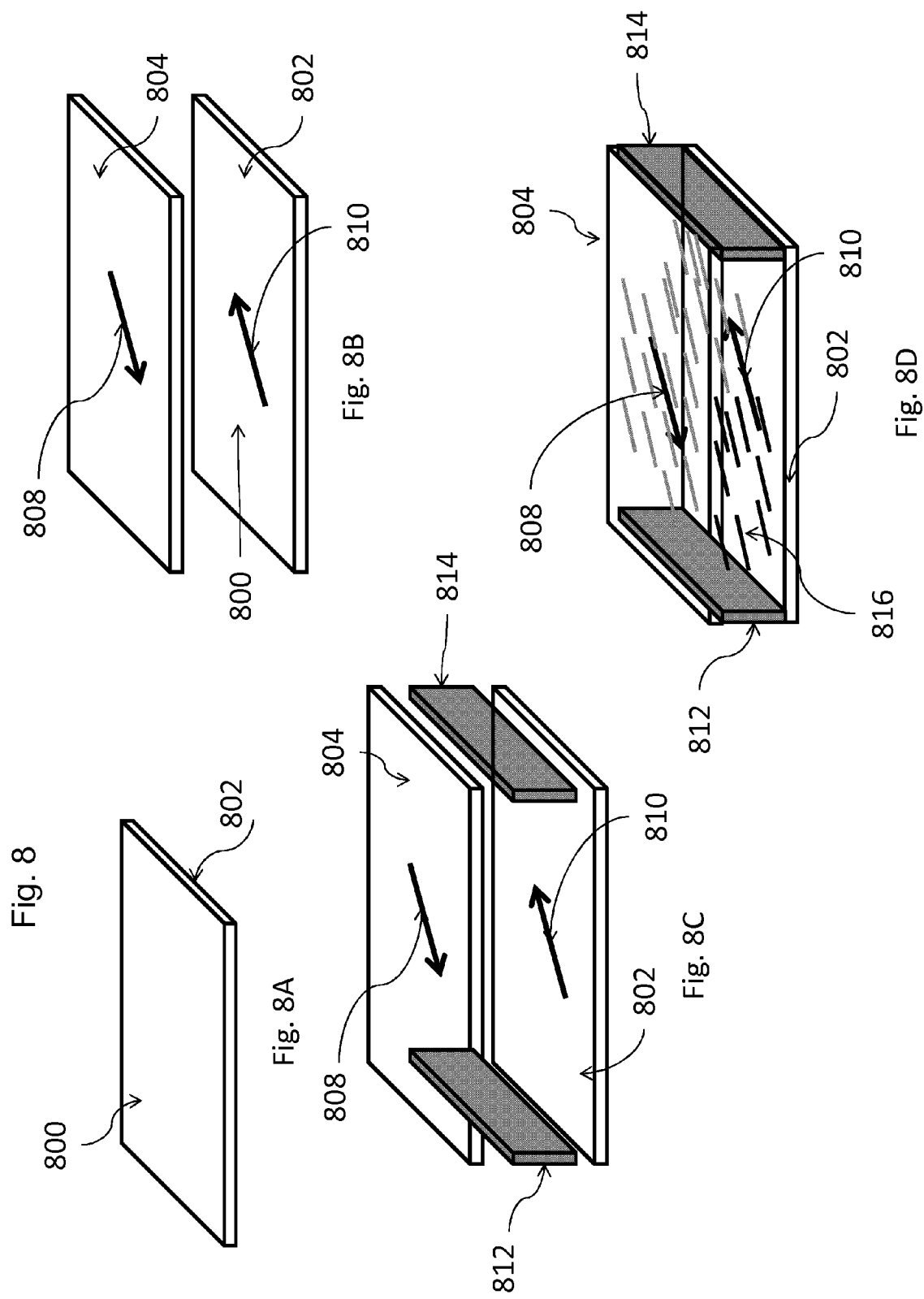
FIGS. 8A, 8B, 8C and 8D show how a spiral plate can be made.

For example, the spiral plate shown in FIG. 8 A to D can be covered with a liquid crystal birefringent material. The directors of the liquid crystal material are preferably parallel to the high thickness side of the spiral plate 800 to minimise discontinuities of alignment of liquid crystal over the spiral plate. To manufacture such a device the substrates 804 and 802 can be replaced with similar substrates (such as glass substrates) that are Indium Tin Oxide (ITO) covered before adding the spiral phase structure on substrate 802 and the alignment layer on substrate 804.

Electrical wiring from driving electronics to the electrodes for the purpose of applying a voltage between the top and bottom electrodes must be provided but is not shown in FIG. 8. Wire connections are then made, for example, by soldering or clamping. When a replica is involved in the manufacture and the replica is manufactured on top of a substrate the electrodes can be patterned prior to replication in order to allow local tilting of the liquid crystal material.

The liquid crystal state can then be switched just like explained with reference to the prism of FIGS. 12A and 12B. If a uniform voltage is applied to the liquid crystal layer, the normal circular illumination pattern (when the spiral plate is constructed to give a circular pattern; see herein above) results, but the circle diameter (and therewith the offset between centre spot and ring) can be controlled by the magnitude of the uniform voltage. At high voltage in the ultimate state, again the spiral plate functions as a transparent plate.

By using patterned electrodes across the cell, much more control of the illumination pattern is enabled. For example, the top electrode can be patterned in the plane of the substrate. By changing the voltage pattern on the liquid crystal layer, the illumination pattern can be controlled. If a voltage pattern is provided, such as a star shape or ellipse, a corresponding illumination pattern can be created. The patterned electrode can also still provide the circular pattern.

A switchable lens using the liquid crystal principle can be made as shown in FIGS. 13A and 13B. The birefringent tunable lens has the same components as the prism (where like numerals represent like components) with the exception that the isotropic parts 1202 are now lens shaped part 1302 instead of the prism shaped parts 1202. Thus there are glass plates 1306 with ITO electrodes 1308 and the alignment layers on the isotropic replica 1302 and the electrode layer 1308 in contact with the liquid crystal layer 1304.

The change of voltage can now be used to alter the focal strength of the lens. Ultimately with large enough voltage applied the lens is switched off such that the device functions as a transparent plate (FIG. 13B).

Figures 13C, 13D:
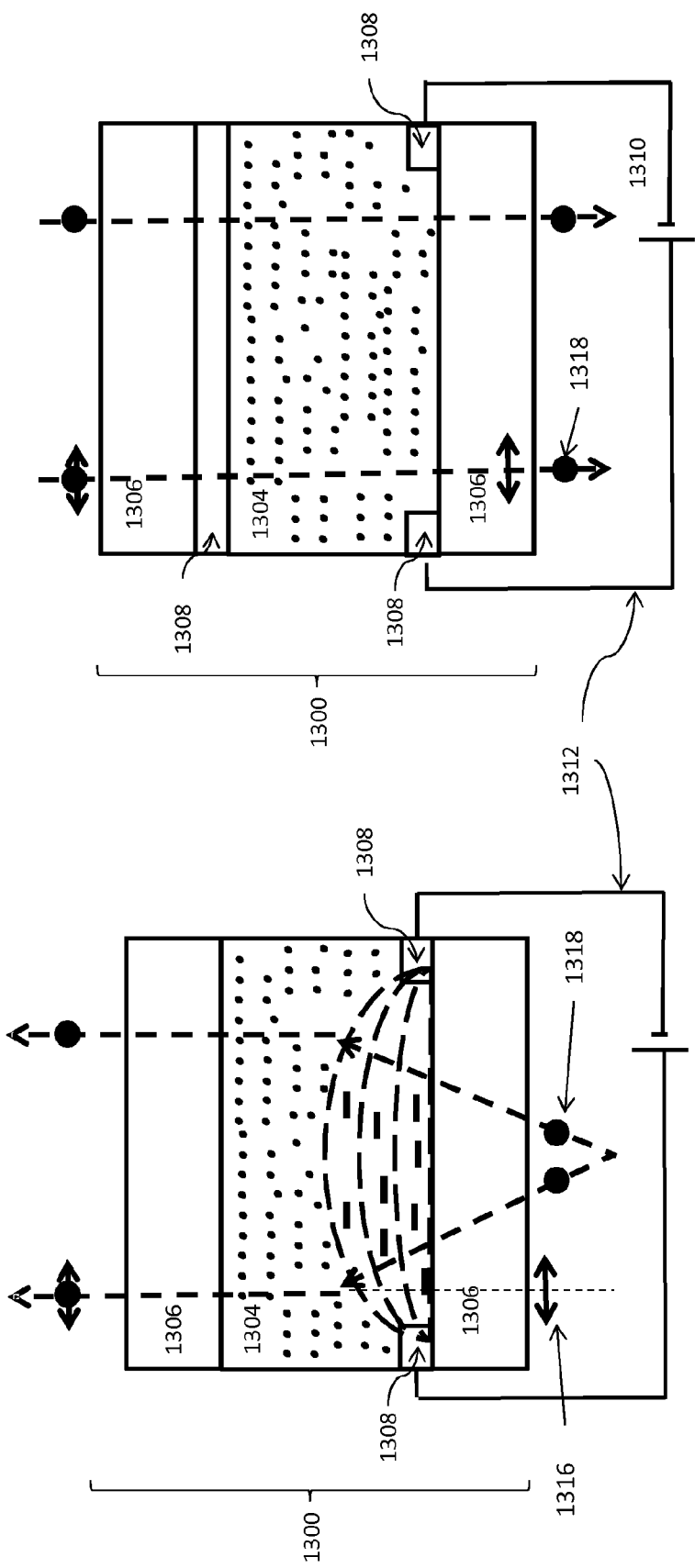
FIGS. 13C and 13D show a birefringent liquid crystal based GRIN lens with adjustable birefringence based on a liquid crystal layer and how it's birefringence can provide different operating modes.

FIGS. 13C and D show a liquid crystal based GRaded INdex (GRIN) device, in this case a lens. The structure of liquid crystal GRIN lenses is known. Such lenses have for example been proposed for use in autostereoscopic displays, and an example can be found in WO2008/126049. Another example is described in U.S. Pat. No. 7,079,203 or in the references described therein. In this type of device the 'birefringent surface' is formed due to partial reorientation of liquid crystal molecules in a cell along curved field lines to form this surface inside the liquid crystal material. In FIG. 13C, the field lines between electrodes 1308 form a curve along which part of the liquid crystal layer molecules 1304 align. The index is therewith graded over the thickness of the device and more or less forms a birefringent surface. Other parts have the same meaning as for FIG. 13A or B. Note that the electrodes 1308 can be elongated to form cylindrical lenses running perpendicular to the plane of drawing, but can also be circular to form lenses with circular aperture.

The invention is not limited to such type switchable arrangements that make use of switchable lenses as described in the example. In fact any switchable element that can switch one polarisation state while treating another one differently, e.g. by leaving that other one unaltered, can be used. Such elements include the combination of a solid state lens with a switchable polarisation rotator (such as regular switchable liquid crystal cell plate).

This type of switchable lens structure has been proposed for use in autostereoscopic displays and comprises a solid birefringent lens and a polarization switching unit. The solid birefringent lens is oriented at 45 degrees to the polarization direction of the linearly polarized light provided to the lens structure. In this way, the lens resolves the incident polarization into two polarization components. An output polarizer is at the exit of the lens structure. In this design, the switchable component can be a planar liquid crystal layer. By switching the planar liquid crystal layer between states, the overall lens arrangement can be switched between a first state in which a lens function is implemented and a second state in which no lens function is implemented. One example can be found in WO 2004/070451. Again, this switching principle can be employed in the optical component for the system of the invention not only of the lenses but also for the other birefringent parts, i.e the prisms and the spiral plate.

Figure 13E:
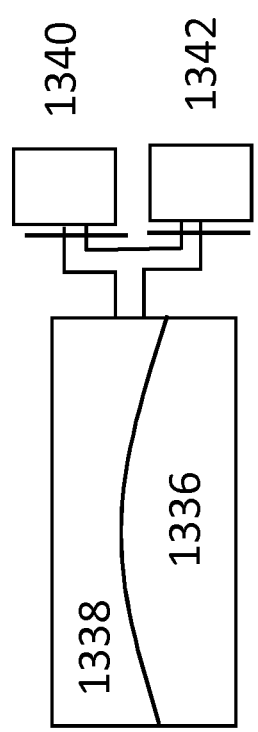
FIG. 13E shows an example with a solid birefringent lens body and a fluid chamber defining the replica part that can be interchanged.

FIG. 13E shows an example with a solid birefringent lens body 1336 and a fluid chamber 1338 defining the replica part that can be interchanged. There are two fluid reservoirs 1340 and 1342 containing different fluids with different refractive index. Replacement of one fluid for the other redefines the birefringent interface between 1336 and 1338. The movement of fluids can be effected by electrowetting or pumping. With electrowetting the fluid reshapes as a consequence of a potential applied to it. There can be more fluid reservoirs, with each fluid reservoir used for a fluid of different refractive index. In another modification, there may be a central solid birefringent lens part, with a fluid chamber both above and below, so that there are two controlled internal refractive index boundaries. Each fluid chamber then can be filled with one of a set of fluids.

A combined variable arrangement can be made. For example the lens of FIG. 13 and the prism of FIG. 12 may be stacked, where one of the glass plates can be shared between both devices. This device can then be operated in one mode to be a lens with lens part as operated in FIG. 13A and prism part as in FIG. 13B or as a prism with lens operated as in FIG. 13B and prism operated as in FIG. 12A. A combined prismatic and lens function can be used. In that case a depth cross section of the material can be scanned. If a second prism is present which operates to deflect in a direction perpendicular to the first one, then a volume of the material can be scanned with spatial offset. All components can still be switched in a mode with no birefringence and hence other measurements of a system can still be deployed without having to remove the component.

With all the arrangements described a variable offset can be provided in a convenient way without moving of the analysis apparatus with respect to the sample to be measured, or without having to replace or move the arrangement or parts of the arrangement. A scan of the material with different offset locations can be conveniently automated using a computer and software to regulate detection and adjustment of offset such that a good data set is recorded over time without further interference of an operator.

It will be apparent from the examples above that the invention can be applied to a variety of known systems, and can be implemented as an additional controllable element in the radiation path to a sample, for example before or after the objective radiation focussing/collection devices of known systems. Thus, the arrangement of the invention can be used without changing the configuration of a standard, highly efficient backscatter analysis system such as one comprising a microscope.

In a microscope, the emitted signal is often detected under 180 degrees called backscatter mode such that, the signal of detection radiation follows the same optical path as that of the excitation radiation for some part within the microscope. In the emission path, spectral information is available from different spatial locations in the sample. This information is disclosed in different polarisation directions, as the materials scatter radiation in all directions and with random polarizations unless they are highly ordered materials.

Not all information can reach the detector. With any of the birefringent arrangements, and assuming that the extraordinary ray would be displaced and the ordinary ray would be unaffected by the birefringent part within the arrangement, the emission from one location in the sample can only reach the detector for one emitted polarisation direction. The other polarisation direction will have an angle that is not directed towards the detector once the birefringent component has been passed (it is off-axis in the microscope). In the examples of FIGS. 2 and 3 for example, this would be the displaced signal coded by ordinary polarised radiation (light).

On its path to the detector the polarisation direction may be altered by retardation plates and other polarisation adjustment components.

Figure 14:
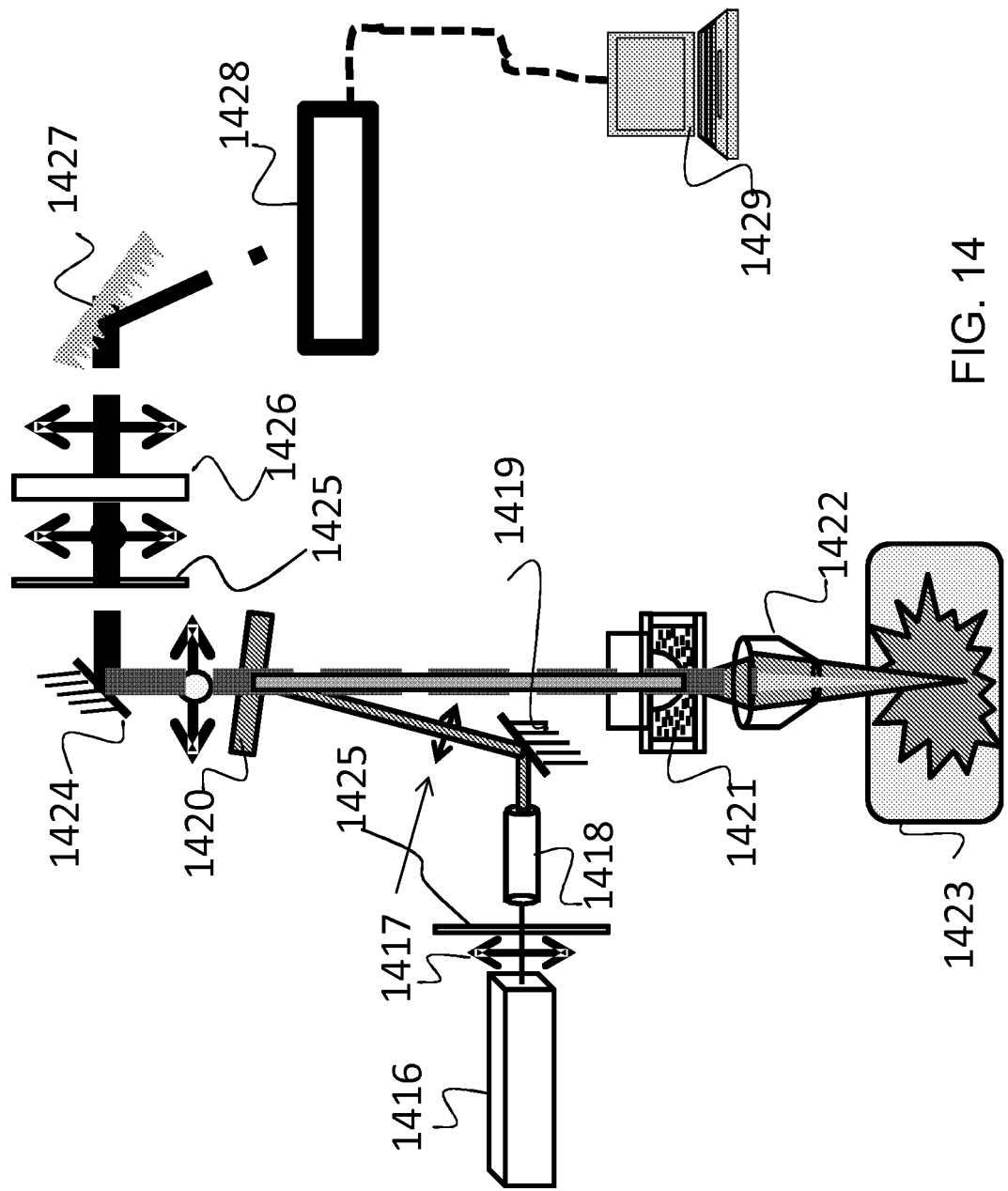
FIG. 14 shows how the arrangement can be part of a backscatter analysis system.

FIG. 14 shows a microscope system for analysing a sample based on fluorescence detection, and in which the variable focus lens arrangement has been employed. That arrangement has been described for example in FIG. 4B where the birefringent part is the one of FIG. 13B that operates as described with reference to FIG. 11B.

The excitation laser source 1416 provides a polarized radiation output with polarization direction 1417. The output beam passes to an optional beam expander 1418 which is used (if needed) to make the beam size appropriate for the lens system, i.e. to e.g. fill the entire aperture at the arrangement with the output beam. The beam is reflected by mirror 1419 to a notch filter, or edge filter 1420 (example of 402 in FIGS. 4A and 4B), which reflects the excitation beam towards the sample. This filter 1420 functions as a wavelength-selective reflector or beam splitter.

The beam passes through the polarization sensitive lens 1421 and is then focussed by the objective lens 1422 onto the sample 1423.

In the way described with regard to FIG. 11, part of the light emitted by the sample and caused by the focussed excitation, is collected by the lens 1422 and passes through the birefringent lens 1421. The polarization component of the emitted light collected and having the polarisation that is different from that of the excitation beam passes through the notch filter 1420, to the mirror 1424, which reflects it to polarizer 1426.

The polarizer 1426 functions as a polarization selective filter and ensures that only the light of the desired polarization (and which has therefore not undergone focusing by the lens 1421) is detected. This polarizer would coincide with the selection polarizer 404 of FIGS. 4A and B, and can operate as described with respect to FIGS. 4A and 4B to select detection radiation from the excitation location or the spatial offset location. Thus, this polarizer 1426 can be used to avoid collection of detection light from the excitation beam focal point having a polarization corresponding to the excitation light, which will also pass to the polarizer 1426 and will add to the contribution of the emitted light signal which is intended to be measured.

The light then passes to a spectrograph grating 1427 and is then detected by a detector 1428 which usually is a CCD or photodiode array. The grating and detector together define the detection unit (spectrometer or photomultiplier). A computer 1429 performs the signal analysis.

FIG. 14 also shows optional retardation plates or switchable liquid crystal cells 1425. One or both of these can be used to control the polarization, for example if the laser polarization is not the desired polarization to be used. For example the one in between laser and beam expander can be used to adjust the polarization orientation to that required to give optimum performance in terms of polarisation splitting function of the polarization sensitive lens 1421. It can correspond to the polarisation adjustment component. The one between mirror 1424 and polariser 1426 can be used for adjustment of polarization if the captured emission light polarization is not optimum for detection by the detector 1428.

The microscope described can be used in general for spatial offset systems such as SORS. As also described with reference to FIG. 4, when implementing a SORS system, the polariser 1426 (part 404 in FIGS. 4A and 4B) is used to discriminate between emission signals that are offset (excitation spot) and non-offset (detection spot). In the same way as explained above, non-offset signals which have the polarization corresponding to the excitation signal will also reach the polarizer. Simple adjustment of the polariser thus allows to record the different spectra from the spot. These spectra can be directly used in data analysis.

In many spectroscopic applications a laser is utilised for excitation. In the majority of situations, this light is already linearly polarised and no additional arrangements need to be made to provide polarised radiation upon excitation. The emitted radiation is then randomly polarized. As explained further below, the lens function means that only a certain polarization of the emitted radiation is directed to the detector, so that effectively the excitation light is of one polarization and the detected emission is of a different polarization.

In an analysis system incorporating the invention regular means appropriate for the radiation principles used (Optical, Fluorescence, Raman etc) in the system can be used for the recording of spectra or analysis of spectra. These may include gratings to split the wavelength parts of an excitation radiation beam onto for example a CCD camera, or a photodiode array or a photomultiplier. For optical principles measurement techniques such as Raman and Fluorescence spectroscopy a CCD camera would be preferred.

Figure 15A:
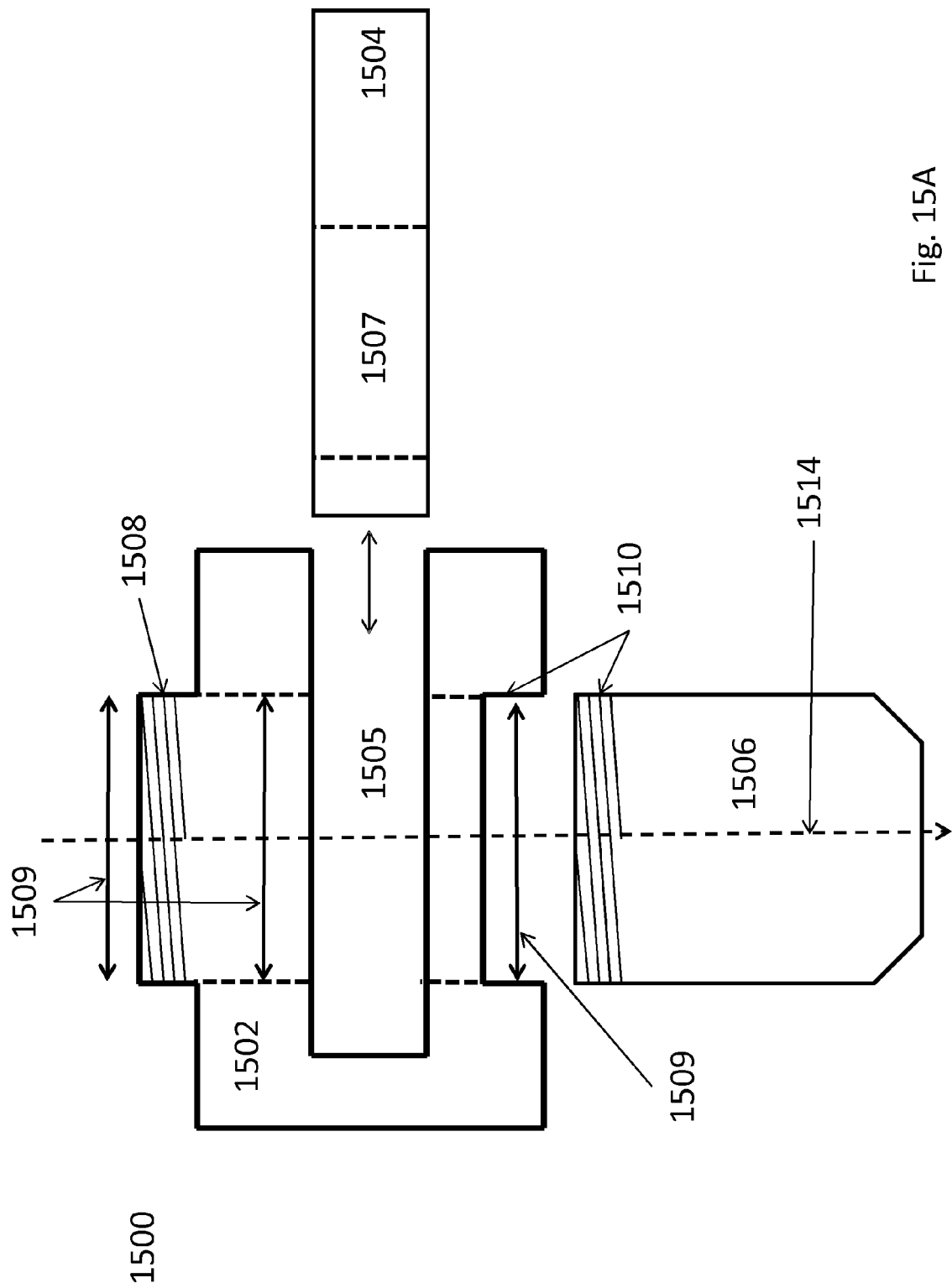
FIGS. 15A and 15B show a side view and top view, respectively, of an implementation of an arrangement as an accessory for an analysis system (e.g. microscope).
Figure 15B:
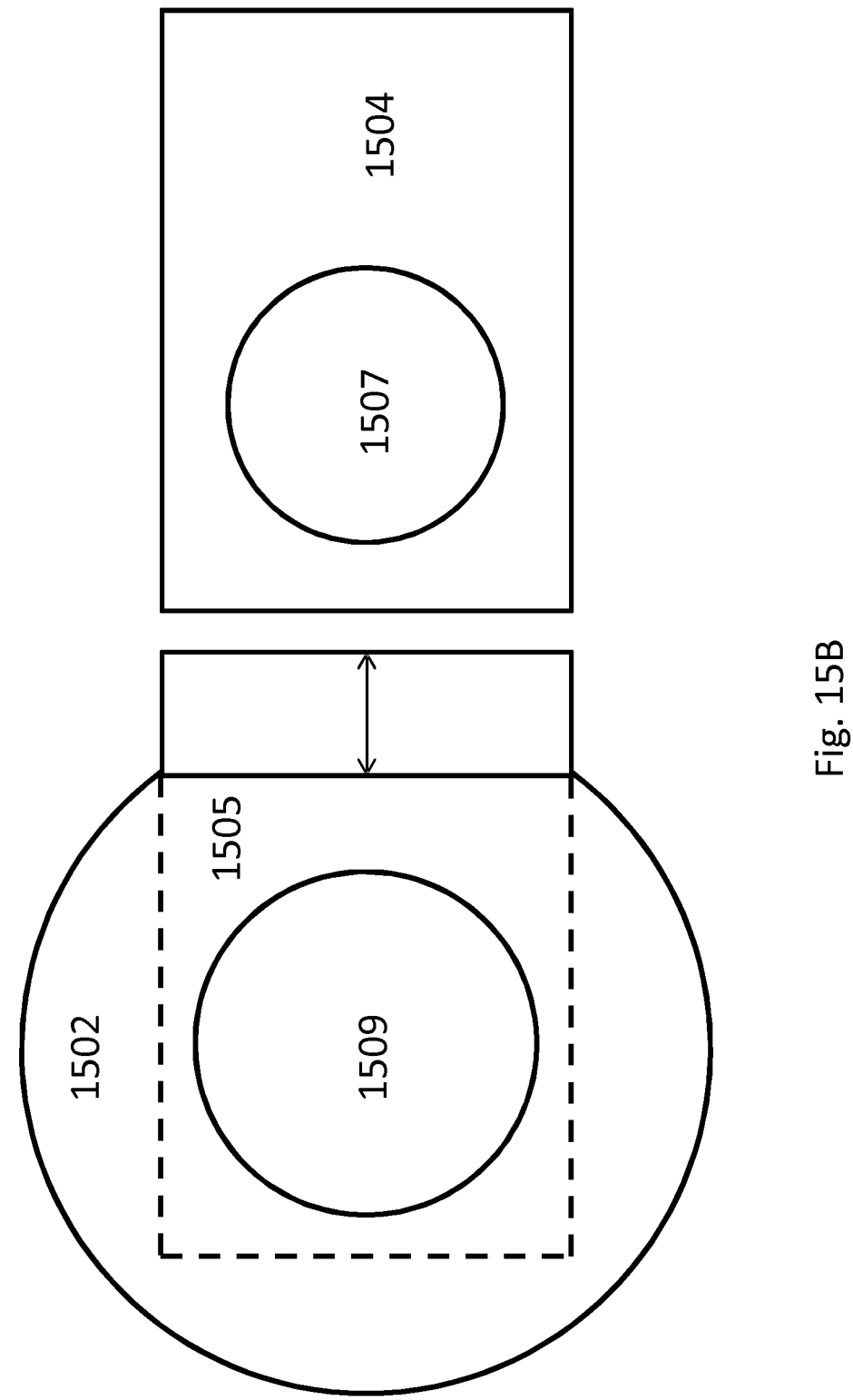

One way to implement the invention in such a microscope is with an arrangement as shown in FIGS. 15A, 15B. and 15C. The arrangement 1500 comprises a holder 1502 having a slot 1505 for holding a component 1504 that includes a polarisation sensitive birefringent part as described herein before. The holder has a circular circumference (others are possible) and from the bottom to top there is a cylindrical pass way 1509 for light to pass through the holder. The holder 1502 has screw thread 1508 on a flange for mounting the holder in a microscopes objective lens carousel (holder). The holder further has screw thread 1510 (not indicated in the drawing) in a recess for accommodating a regular microscope objective 1506 that also has screw thread 1510. When the component 1504 is inserted in the holder 1502, light 1514 can enter the holder through one of the openings 1509, travel through the component cylindrical opening 1507, enter the objective lens and leave the objective lens towards a sample. The component 1504 can accommodate the birefringent part according to the invention such that it occupies the opening 1507. In this case the component 1504 can slide in and out of the holder so that it may be replaced for another one. Alternatively, the ensemble is of fixed nature.

The component 1504 may comprise sandwiches of the birefringent parts of the invention such that these are in series in the light path of the arrangement, or the component 1504 may be extended such that it has multiple openings 1507 each having a single birefringent part of the invention such that these can be successively placed in series with the opening 1509 in the holder by a simple slider action. A rotational variant having a carousel can be used also. The holder 1502 may have two slots 1505 in series in the direction of the light path each of these housing a component 1504. That gives independent control of birefringent part choice.

Figure 15C:
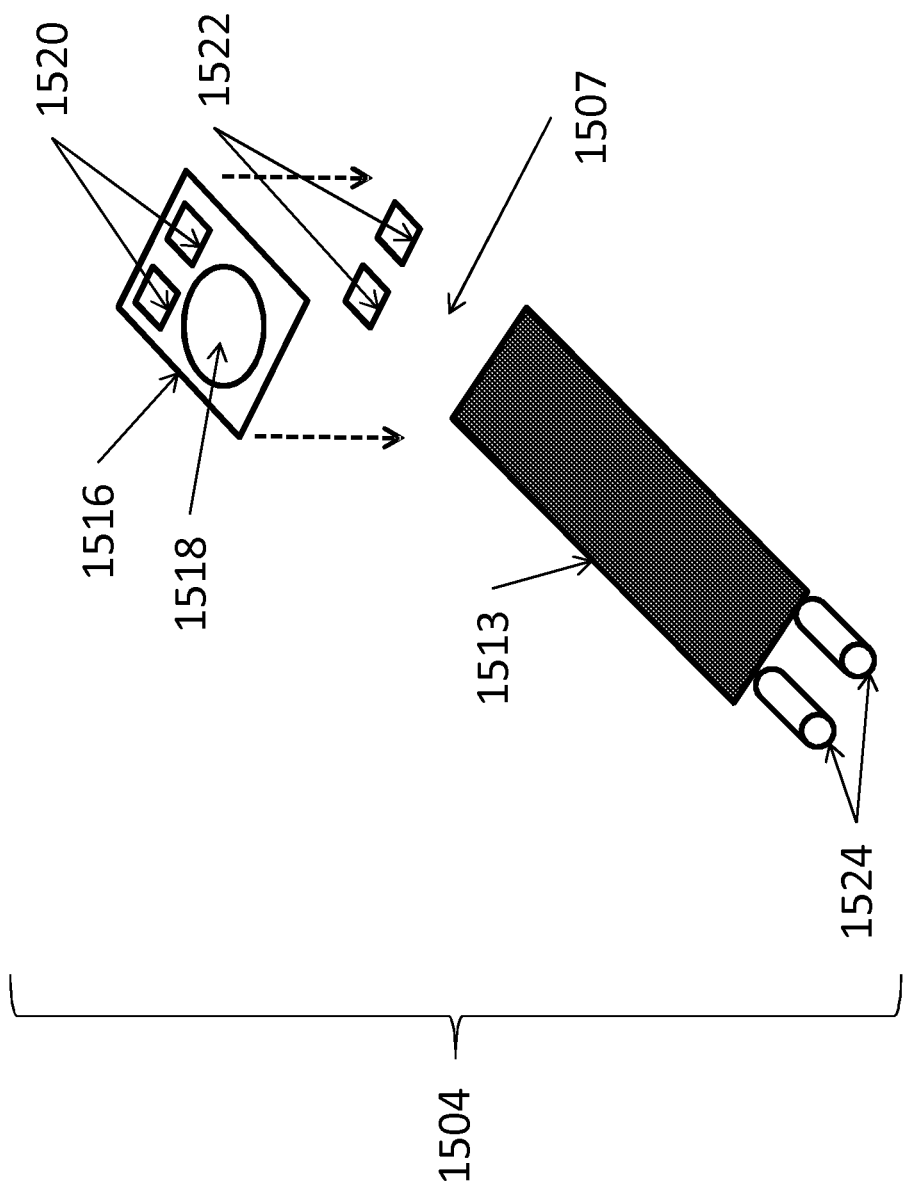
FIG. 15C shows how a switchable birefringent component can be part of a holder that is removable from an arrangement or analysis system according to the invention.

Preferably, the component 1504 is constructed as in FIG. 15C to accommodate electrically driven adjustable birefringent parts such as those described herein. Thus, the component 1504 includes a component body 1513 having the opening 1507 as a light path. The component 1504 includes a birefringent part 1516 of the liquid crystal type as described herein before. The electrodes of the part 1516 can be contacted using contact pads 1520 on the bottom side of the part 1516. The birefringent part has an aperture 1518 for passing the light. The aperture 1518 overlies the opening 1507

The body 1513 accommodates electrical contact pads 1522 for connecting to the contact pads 1520. The contact pads 1522 are in turn connected to the electrical plugs 1524 for electrical connection to driving devices. Thus by means of the electrical contacts 1524 the driving voltages can be supplied to the adjustable birefringent parts. The driving may be supplied by internal microscope electronics or even outside electronic sources. These may be computer steered or manual.

Other ways of electrical contact design may be used.

Again multiple such components 1504 can be accommodated in multiple slots of a holder 1502.

Although not shown, the holder and component may have markers for indicating proper polarisation direction alignment.

In summary, an arrangement having a birefringent component is provided for use in spatial offset measurements and analysis systems. The birefringent optical arrangement provides different directional control of the excitation signal relative to the emission signal, so that offset between an excitation and emission location on a sample can be controlled for both or only one of the excitation signal relative to the emission signal.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. An arrangement for use in performing spatial offset analysis of a medium, wherein the arrangement comprises:
a birefringent component including a birefringent material, the birefringent component comprising a first side adjacent a detector and a second side adjacent the medium, the birefringent component configured to first manipulate a beam of primary radiation of a first polarization that is incident on the first side, the first manipulation directing the beam of primary radiation to a first location of the medium, the birefringent component further configured to second manipulate at least part of a beam of secondary radiation of a second polarization incident on the second side from a second location of the medium, the secondary radiation based on irradiation of the medium by the primary radiation, the second manipulation directing the at least part of the beam of secondary radiation to the detector, the second location being at least partially different from the first location, wherein the effect of the first manipulation is different from the effect of the second manipulation due to the first polarization being different from the second polarization.

2. The arrangement of claim 1, wherein the birefringent material comprises an ordinary refractive index and an extraordinary refractive index and a further material having a further refractive index that is different from at least one of the ordinary refractive index and the extraordinary refractive index, wherein the birefringent material and the further material define a birefringent surface for providing the first manipulation, the second manipulation, or a combination of the first and second manipulations.

3. The arrangement of claim 2, wherein the further material is part of the birefringent component and the further refractive index is equal to one of the ordinary refractive index and the extraordinary refractive index.

4. The arrangement of claim 2, wherein the birefringent surface comprises a plurality of birefringent sub-surfaces, wherein each of the birefringent sub-surfaces contains an imaginary radial line extending radially from an axis, the axis being oriented perpendicular to an imaginary plane and each of the birefringent sub-surfaces is inclined with respect to the imaginary plane over an inclination angle, the inclination angle being defined between an imaginary line that is perpendicular to the imaginary radial line, and the line constructed by perpendicular projection of the imaginary line onto the imaginary plane.

5. The arrangement of claim 1, wherein the birefringent component is controllable for adjustment of the first manipulation the second manipulation, or a combination of the first and second manipulations.

6. The arrangement of claim 5, wherein the birefringent material comprises a liquid crystal material and at least one electrode for applying an electric field over at least a part of the liquid crystal material for controlling the adjustment of the first manipulation, the second manipulation, or a combination of the first and second manipulations.

7. The arrangement of claim 6, wherein the arrangement has an operating mode in which the birefringent component third manipulates a beam of primary radiation, the third manipulation directing the beam of primary radiation to the first location, the birefringent component further configured to fourth manipulate the at least part of a beam of secondary radiation from the second location, wherein the first location and the second location are the same, the birefringent component configured to be controlled such that the third manipulation and the fourth manipulation are the same.

8. The arrangement of claim 5, wherein the arrangement comprises a polarization adjustment component for adjusting the polarization of primary radiation of the beam of primary radiation before the primary radiation is incident on the birefringent component, therewith providing the controlling of the adjustment of the first manipulation, the second manipulation, or a combination of the first and second manipulations.

9. The arrangement of claim 5, wherein the birefringent material comprises an ordinary refractive index and an extraordinary refractive index and a further material having a further refractive index that is different from at least one of the ordinary refractive index and the extraordinary refractive index, wherein the birefringent material and the further material define a birefringent surface for providing the first manipulation, the second manipulation, or a combination of the first and second manipulations, wherein the further material comprises a solid material for defining the shape of the birefringent surface and wherein the birefringent material comprises a liquid crystal material and the arrangement comprises at least one electrode for applying an electric field over at least a part of the liquid crystal material for controlling the adjustment of the first manipulation, the second manipulation, or a combination of the first and second manipulations.

10. The arrangement of claim 5, wherein the birefringent material comprises an ordinary refractive index and an extraordinary refractive index and a further material having a further refractive index that is different from at least one of the ordinary refractive index and the extraordinary refractive index, wherein the birefringent material and the further material define a birefringent surface for providing the first manipulation, the second manipulation, or a combination of the first and second manipulations, wherein the birefringent material comprises a solid material for defining the shape of the birefringent surface and wherein the further material comprises a fluid material contained within a compartment having a boundary formed by the birefringent surface such that the fluid material is in contact with the birefringent material, wherein the composition of the fluid material in contact with the birefringent material is adjustable.

11. The arrangement claim 1, wherein the birefringent surface comprises a shape such that the first manipulation, the second manipulation, or a combination of the first and second manipulations comprise any one or a combination of deflection or change of parallelism of a beam of radiation.

12. The arrangement of claim 11, wherein the birefringent surface comprises a birefringent prism surface for providing any one or a combination of the deflection or a birefringent lens surface for providing the change of parallelism of a beam of radiation.

13. The arrangement of claim 1, wherein the arrangement comprises a further birefringent component, the further birefringent component configured to additionally manipulate the beam of primary radiation, the further birefringent component further configured to additionally manipulate the at least part of the beam of secondary radiation, wherein the effect of the additional manipulation of the beam of primary radiation is different from the effect of the additional manipulation of the at least part of the beam of secondary radiation due to the first polarization being different from the second polarization.

14. The arrangement of claim 1, further comprising a pinhole component comprising a pinhole for passing the at least part of the beam of secondary radiation.

15. The arrangement of claim 1, further comprising a collection component for convergence of the at least part of the beam of the secondary radiation.

16. The arrangement of claim 1, further comprising a beam splitter arranged in between the birefringent component and the detector, the beam splitter being arranged for passing the at least part of the beam of the secondary radiation towards the detector and for directing any primary radiation directed by the birefringent component to the beam splitter substantially away from the detector.

17. The arrangement of claim 1, wherein the arrangement further comprises a polarization selective filter arranged in between the birefringent component and the detector for controlling the intensity of the secondary radiation that is incident on the detector.

18. The arrangement claim 17, further comprising a holder for holding the birefringent component, the holder being removable from the arrangement.

19. The arrangement of claim 18, wherein the holder is moveable with respect to the arrangement such that one or more birefringent components can be positioned to provide the first manipulation, the second manipulation, or a combination of the first and second manipulations at any one time.

20. The arrangement of claim 1, wherein the birefringent component is removable from the arrangement.

21. The arrangement of claim 1, wherein the arrangement is an accessory for an analysis system that is configured to be detachable from the analysis system.

22. An analysis system comprising:
a radiation source configured to provide a beam of primary radiation of a first polarization;
a detector;
an arrangement comprising a birefringent component that includes a birefringent material, the birefringent component configured to first manipulate the beam of primary radiation, the first manipulation directing the beam of primary radiation to a medium at a first location, the birefringent component further configured to second manipulate at least part of a beam of secondary radiation of a second polarization collected from a second location of the medium, the secondary radiation based on irradiation of the medium by the primary radiation, the second manipulation directing the at least part of the beam of secondary radiation to the detector, the second location being at least partially different from the first location, wherein the effect of the first manipulation is different from the effect of the second manipulation due to the first polarization being different from the second polarization.

23. The analysis system of claim 22, wherein the arrangement is an accessory to the analysis system, wherein the accessory is configured to be detachable from the analysis system.

24. The analysis system of claim 22, wherein the analysis system is any one of, or a combination of: a microscope, a backscatter microscope, a fluorescence detection system, a phosphorescence detection system, a RAMAN spectrometer, a near-IR and/or IR spectrometer, a UV spectrometer, a microwave detection system, wherein the microscope or the backscatter microscope can be a part of the detection systems or the spectrometers.

25. The analysis system of claim 22, further comprising: a beam splitter arranged in between the birefringent component and the detector, the beam splitter being arranged for passing the at least part of the beam of the secondary radiation towards the detector and for directing any primary radiation directed by the birefringent component to the beam splitter substantially away from the detector and the beam splitter being further arranged for directing the primary radiation from the source to the birefringent component;
  a polarization adjustment component for adjusting the polarization of the primary radiation before the primary radiation is incident on the birefringent component; and
  a polarization selective filter arranged in between the birefringent component and the detector for controlling the intensity of the secondary radiation that is incident on the detector.

26. The analysis system of claim 22, further comprising a unit for data analysis of spatial offset detection measurements.

27. The analysis system of claim 22, further comprising a holder for holding the birefringent component, the holder being removable from the arrangement.

28. The analysis system of claim 27, wherein the birefringent component is removable from the arrangement, and wherein the holder is moveable with respect to the arrangement such that one or more birefringent components can be positioned to provide the first manipulation, the second manipulation, or a combination of the first and second manipulations at any one time.

29. A method for performing spatial offset detection, the method comprising:
  manipulating at a birefringent component a beam of primary radiation that passes through birefringent material of the birefringent component, the manipulation directing the beam of primary radiation to a medium at a first location, the primary radiation comprising a first polarization, the birefringent component comprising birefringent material; and
  manipulating at the birefringent component at least part of a beam of secondary radiation having a second polarization that is emitted from a second location of the medium, the emission based on irradiation of the medium by the primary radiation, the manipulation of the at least part of the beam of secondary radiation directing the at least part of the beam of secondary radiation to a detector, the second location being at least partially different from the first location,
  wherein the effect of the manipulation of the beam of primary radiation is different from the effect of the manipulation of the at least part of the beam of secondary radiation due to the first polarization being different from the second polarization.

30. The method of claim 29, further comprising adjusting a relative contribution of secondary radiation of the first polarization and the secondary radiation of the second polarization incident on the detector, between consecutive detections of secondary radiation.

31. The method of claim 30, further comprising:
  detecting the secondary radiation with the second polarization from the second location;
  controlling the birefringent component to shift the second location while keeping the first location constant; and
  detecting secondary radiation with the second polarization from the shifted second location.

32. The method of claim 29, further comprising adjusting the polarization of primary radiation of the beam of primary radiation before the primary radiation is incident on the birefringent component.

33. The method of claim 29, further comprising applying an electric field over at least a part of the birefringent material.

34. The method of claim 29, further comprising causing the convergence of the at least part of the beam of the secondary radiation.

* * * * *